(12) United States Patent
Sano et al.

(10) Patent No.: US 7,144,374 B2
(45) Date of Patent: Dec. 5, 2006

(54) CUFF FOR BLOOD PRESSURE MONITOR

(75) Inventors: Yoshihiko Sano, Kyoto (JP); Hiroshi Kishimoto, Kyoto (JP); Hiromichi Karo, Kyoto (JP); Takahide Tanaka, Otsu (JP)

(73) Assignee: Omron Healthcare Co., Ltd., Kyoto (JP)

( * ) Notice: Subject to any disclaimer, the term of this patent is extended or adjusted under 35 U.S.C. 154(b) by 0 days.

(21) Appl. No.: 11/216,099

(22) Filed: Sep. 1, 2005

(65) Prior Publication Data

US 2006/0047206 A1 Mar. 2, 2006

(30) Foreign Application Priority Data

Sep. 2, 2004 (JP) ............... 2004-255979

(51) Int. Cl.
*A61B 5/02* (2006.01)
(52) U.S. Cl. .............. 600/499; 600/490; 600/491
(58) Field of Classification Search ........ 600/490–503, 600/481, 485; 6/201–203
See application file for complete search history.

(56) References Cited

U.S. PATENT DOCUMENTS

| | | | | |
|---|---|---|---|---|
| 4,109,646 A | * | 8/1978 | Keller | 600/499 |
| 4,248,242 A | * | 2/1981 | Tamm | 600/491 |
| 4,526,165 A | * | 7/1985 | Mielnik et al. | 128/882 |
| 4,549,550 A | * | 10/1985 | Kami | 600/499 |
| 4,790,325 A | * | 12/1988 | Lee | 600/490 |
| 5,595,180 A | * | 1/1997 | Ogura et al. | 600/499 |
| 2004/0010198 A1 | * | 1/2004 | Yamakoshi et al. | 600/499 |
| 2004/0186385 A1 | * | 9/2004 | Mochizuki | 600/499 |
| 2005/0182332 A1 | * | 8/2005 | Sano et al. | 600/499 |
| 2005/0187485 A1 | * | 8/2005 | Fumuro et al. | 600/499 |
| 2005/0192501 A1 | * | 9/2005 | Sano et al. | 600/499 |
| 2005/0228302 A1 | * | 10/2005 | Dalgaard et al. | 600/499 |
| 2005/0283085 A1 | * | 12/2005 | Inoue et al. | 600/499 |
| 2005/0288597 A1 | * | 12/2005 | Kishimoto et al. | 600/499 |

FOREIGN PATENT DOCUMENTS

| | | |
|---|---|---|
| JP | 61-238229 | 10/1986 |
| JP | 7-124127 | 5/1995 |
| JP | 7-136132 | 5/1995 |
| JP | 10-033489 | 2/1998 |
| JP | 10-033490 | 2/1998 |
| JP | 2002-209858 | 7/2002 |
| JP | 2003-210423 | 7/2003 |

* cited by examiner

*Primary Examiner*—Charles A Marmor, II
*Assistant Examiner*—N Natnithithadha
(74) *Attorney, Agent, or Firm*—Morrison & Foerster LLP

(57) ABSTRACT

A cuff for a blood pressure monitor includes a cuff main unit wound around a measurement site of a living body, and a handle provided on the outer peripheral surface of the cuff main unit and gripped with a hand for fitting the cuff. The cuff main unit includes a cover member in which an air bag for pressing the living body and a curled elastic member wound annularly on the outside of the air bag and radially changeable in size are contained, and a diameter increasing/decreasing mechanism for increasing/decreasing a diameter of the curled elastic member. The handle has a push-button for increasing/decreasing the diameter of the curled elastic member by switching an operation of the diameter increasing/decreasing mechanism. This can provide a cuff for a blood pressure monitor permitting easy mounting/dismounting with respect to the measurement site of the living body.

9 Claims, 14 Drawing Sheets

CUFF FOR BLOOD PRESSURE MONITOR

BACKGROUND OF THE INVENTION

1. Field of the Invention

The present invention relates to a cuff for a blood pressure monitor, and more particularly to a cuff for a blood pressure monitor provided with an elastic member for securing a fluid bag to a living body.

2. Description of the Background Art

To measure a blood pressure value, generally, a cuff provided with a fluid bag for pressing an artery located within a living body is wound around the body surface, and arterial pressure pulse waves caused in the artery by inflation/deflation of the fluid bag are detected to measure the blood pressure value. Here, the cuff refers to a band-shaped structure having a bladder, which can be wound around a part of a living body, for use in measurement of arterial pressure of an upper limb, a lower limb or the like by introducing fluid such as gas or liquid into the bladder. Thus, the cuff represents the concept including the fluid bag as well as members for winding the fluid bag around the living body. Particularly, the cuff wound around and fitted on an arm is also called an arm band or a manchette.

When mounting the cuff for a blood pressure monitor, it is necessary to unfailingly wind the cuff main unit around the living body in order for the fluid bag to be reliably secured to the measurement site of the living body. In the case of a conventional cuff for a blood pressure monitor, however, the infallible winding is not always guaranteed because a subject of the measurement is entrusted with the winding operation. Variation in winding operation leads to variation in measurement value, making it difficult to realize accurate and stable measurement of the blood pressure values.

To realize the reliable winding of the cuff main unit, a cuff for a blood pressure monitor that has an elastic member called a curled elastic member contained in the cuff main unit in addition to a fluid bag is known (see, e.g., Japanese Patent Laying-Open Nos. 2003-210423, 61-238229, 2002-209858). The curled elastic member serves to retain the annular shape of the cuff main unit, and is wound annularly on the outside of the fluid bag inside the cuff main unit, so as to make the cuff main unit radially changeable in size. When the cuff for a blood pressure monitor having such a curled elastic member is fitted to the living body, the curled elastic body presses the fluid body against the living body at an appropriate pressing force to secure the same on the measurement site, so that reliable winding of the fluid body around the living body can be realized repeatedly.

A specific configuration of the cuff for a blood pressure monitor provided with the curled elastic member as described above and a way of winding the same are disclosed, e.g., in Japanese Patent laying-Open Nos. 10-033490, 07-136132, 10-033489, and 07-124127. Hereinafter, the configurations and winding manners of the cuffs for a blood pressure monitor disclosed in these publications will be described.

Firstly, in the cuff for a blood pressure monitor of a conventional example 1 disclosed in Japanese Patent Laying-Open No. 10-033490, the cuff main unit containing an air bag and a curled elastic member therein is inserted through a ring member to fold it back at a prescribed position. A sheet-shaped joining member such as a velcro fastener is provided on the outer surface of the cuff main unit. With the cuff for a blood pressure monitor having such a configuration, after the cuff main unit is wound around a measurement site, it is folded back outward at the position defined by the ring member, and the folded part of the cuff main unit is secured to the outer surface of the unfolded part thereof by means of the sheet-shaped joining member.

In the cuff for a blood pressure monitor of a conventional example 2 disclosed in Japanese Patent Laying-Open No. 07-136132, the cuff main unit containing an air bag and a curled elastic member therein has a pivotable operation plate on one end, and has a ring on the other end, which can be engaged with a hook provide on the inner surface of the operation plate. With the cuff for a blood pressure monitor having such a configuration, after the cuff main unit is wound around a measurement site, the ring is engaged with the hook provided on the inner surface of the operation plate, and while the engagement is being maintained, the operation plate is pivoted to secure the cuff main unit to the living body.

In the cuff for a blood pressure monitor of a conventional example 3 disclosed in Japanese Patent Laying-Open No. 10-033489, the cuff main unit is formed of an inner binding belt and an outer binding belt. The inner binding belt contains an air bag and a curled elastic member therein, and is in a cylindrical form and expandable as is elastically wound around a measurement site. The outer binding belt is less elastic and wound over the inner binding belt. With the cuff for a blood pressure monitor having such a configuration, the measurement site of the living body is inserted through the inner binding belt of the cylindrical form, with the outer binding belt yet to be wound. After the inner binding belt is brought into close contact with the living body, the outer binding belt is fastened from above the inner binding belt to secure the cuff main unit to the living body.

In the cuff for a blood pressure monitor of a conventional example 4 disclosed in Japanese Patent Laying-Open No. 07-124127, a cover unit halved in a circumferential direction is provided on the outside of a curled elastic member. The halves of the cover unit are provided with tab members at the connecting portion thereof, to protrude outward from the respective halves. The curled elastic member is fixed to the inner peripheral surfaces of the halves of the cover unit. With the cuff for a blood pressure monitor having such a configuration, the tab members are pinched with fingers to narrow the distance therebetween so as to increase the diameter of the curled elastic member in opposition to the elastic force thereof, and while maintaining the diameter-increased state, the cuff main unit is applied to a measurement site. Thereafter, the fingers having pinched the tab members are released so as to secure the cuff main unit to the living body.

However, with any of the cuffs for a blood pressure monitor of the above-described conventional examples 1 through 4, the cuff-winding operation is considerably troublesome, since the curled elastic member needs to be configured to maintain a diameter smaller than that of a measurement site of the living body in the non-fitted state, such that the curled elastic member when fitted can reliably press the air bag against the measurement site of the living body. More specifically, upon fitting of the cuff main unit, the curled elastic member in the diameter-decreased state needs to be increased in diameter so as to be fitted to the measurement site of the living body. It is this diameter-increasing operation of the curled elastic member that makes the cuff fitting operation troublesome. Particularly, in the case of a cuff for a blood pressure monitor for household use, the subject himself/herself needs to wind the cuff main unit around one arm using the other hand, which is accompanied by very troublesome operations of spreading the cuff main unit in the diameter-decreased state and mounting the same on the arm that should be done with a single hand. The operation of dismounting the cuff main unit after measurement is also burdensome.

To alleviate such troublesomeness, the cuff for a blood pressure monitor of the above-described conventional example 4 is provided with the tap members on the outer peripheral surface of the cuff main unit to facilitate the operation of spreading the curled elastic member. With this configuration, however, it is necessary to put certain power to the fingertips for sufficiently increasing the diameter of the curled elastic member. Thus, the mounting/dismounting operations of the cuff main unit are still troublesome for elderly people and women relatively weak in physical strength.

SUMMARY OF THE INVENTION

An object of the present invention is to provide a cuff for a blood pressure monitor permitting easy mounting/dismounting with respect to a measurement site of the living body.

A cuff for a blood pressure monitor according to the present invention is fitted to a measurement site of a living body for measurement of a blood pressure value, and includes: a cuff main unit wound around the measurement site to be fitted on the living body; and a handle provided on an outer peripheral surface of the cuff main unit and gripped with a hand for fitting of the cuff. The cuff main unit has a fluid bag for pressing the living body, an elastic member wound annularly on the outside of the fluid bag and changeable in size in a radial direction, and a diameter increasing/decreasing mechanism for increasing/decreasing a diameter of the elastic member. In the cuff for a blood pressure monitor of the present invention, a manipulation portion for increasing/decreasing the diameter of the elastic member by switching an operation of the diameter increasing/decreasing mechanism is provided at the handle or at the cuff main unit in the vicinity of the handle.

In the cuff for a blood pressure monitor of the present invention described above, the manipulation portion is preferably formed of a push-button. In this case, preferably, the diameter increasing/decreasing mechanism operates to increase the diameter of the elastic member in association with depression of the push-button, and operates to decrease the diameter of the elastic member in association with release of the depression of the push-button.

Alternatively, in the cuff for a blood pressure monitor of the present invention described above, the manipulation portion is preferably formed of a lever. In this case, preferably, the diameter increasing/decreasing mechanism operates to increase the diameter of the elastic member in association with manipulation of the lever, and operates to decrease the diameter of the elastic member in association with release of the manipulation of the lever.

In the cuff for a blood pressure monitor of the present invention described above, preferably, the diameter increasing/decreasing mechanism includes a diameter-decreased state maintaining mechanism for maintaining the elastic member in a diameter-decreased state by restricting elastic deformation of the elastic member in a radially outward direction, a diameter-decreased state releasing mechanism for releasing the elastic member to a diameter-increased state by releasing the restriction of the elastic deformation of the elastic member by the diameter-decreased state maintaining mechanism, and a diameter-forcibly-decreasing mechanism for forcibly decreasing the diameter of the elastic member in opposition to an elastic force of the elastic member in the diameter-increased state, and each of the diameter-decreased state maintaining mechanism, the diameter-decreased state releasing mechanism and the diameter-forcibly-decreasing mechanism is configured to work in association with manipulation of the manipulation portion. In this case, preferably, the manipulation portion is formed of a push-button provided at the handle, and the diameter-decreased state releasing mechanism works in association with depression of the push-button to cause the elastic member having been maintained in the diameter-decreased state by the diameter-decreased state maintaining mechanism to be released to the diameter-increased state, and the diameter-forcibly-decreasing mechanism and the diameter-decreased state maintaining mechanism work in association with release of the depression of the push-button to forcibly decrease the diameter of the elastic member and to cause the elastic member forcibly decreased in diameter to be maintained in the diameter-decreased state.

In the cuff for a blood pressure monitor of the present invention described above, preferably, the diameter increasing/decreasing mechanism includes a fastening band wound on the outside of the elastic member, a pair of movable members attached to respective ends in the circumferential direction of the fastening band and movable along the circumferential direction of the cuff main unit, an elastic body elastically connecting the movable members, and a lock member working in association with manipulation of the manipulation portion and capable of locking the movable members in an immovable manner in opposition to an elastic force of the elastic body.

In the cuff for a blood pressure monitor of the present invention described above, preferably, the diameter increasing/decreasing mechanism includes a diameter-forcibly-increasing mechanism for forcibly increasing the diameter of the elastic member in opposition to an elastic force of the elastic member in a radially inward direction, and the diameter-forcibly-increasing mechanism works in association with manipulation of the manipulation portion. In this case, preferably, the manipulation portion is formed of a lever provided at the handle, and the diameter-forcibly-increasing mechanism works in association with manipulation of the lever to forcibly increase the diameter of the elastic member in the diameter-decreased state, and the diameter-forcibly-increasing mechanism stops working in association with release of the manipulation of the lever, so that the elastic member in the diameter-increased state is decreased in diameter.

In the cuff for a blood pressure monitor of the present invention described above, preferably, the diameter increasing/decreasing mechanism includes a line-shaped or band-shaped member provided along the outside of the elastic member and having its ends attached to the corresponding ends in the circumferential direction of the elastic member, and a pull-up mechanism capable of pulling up an approximately central portion of the line-shaped or band-shaped member in a direction coming apart from the outer surface of the elastic member. In this case, preferably, the elastic member includes at least three segments arranged along the circumferential direction, and elastic bodies each located between the neighboring segments and connecting them with each other, and the line-shaped or band-shaped member has its ends attached to the pair of segments located at the respective ends in the circumferential direction of the elastic member.

According to the present invention, it is possible to provide a cuff for a blood pressure monitor that can readily be mounted to and dismounted from a measurement site of the living body.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 3A shows a schematic top plan view of and FIG. 3B shows a schematic perspective view of the mechanism in the non-fitted state.

FIG. 4A shows a schematic top plan view of and FIG. 4B shows a schematic perspective view of the mechanism in the diameter-increased state.

FIG. 6A shows a schematic top plan view of the mechanism in the course of the diameter-decreasing operation and FIG. 6B shows a schematic top plan view of the mechanism upon completion of the diameter-decreasing operation.

FIG. 12A shows the state where the lever is not operated and FIG. 12B shows the state where the lever is operated.

DESCRIPTION OF THE PREFERRED EMBODIMENTS

Hereinafter, embodiments of the present invention will be described in detail with reference to the drawings. In the following embodiments, as the cuff for a blood pressure monitor, one for a so-called upper arm blood pressure monitor that is fitted to the upper arm upon measurement of a blood pressure value will be described by way of example.

FIRST EMBODIMENT

Figure 1:
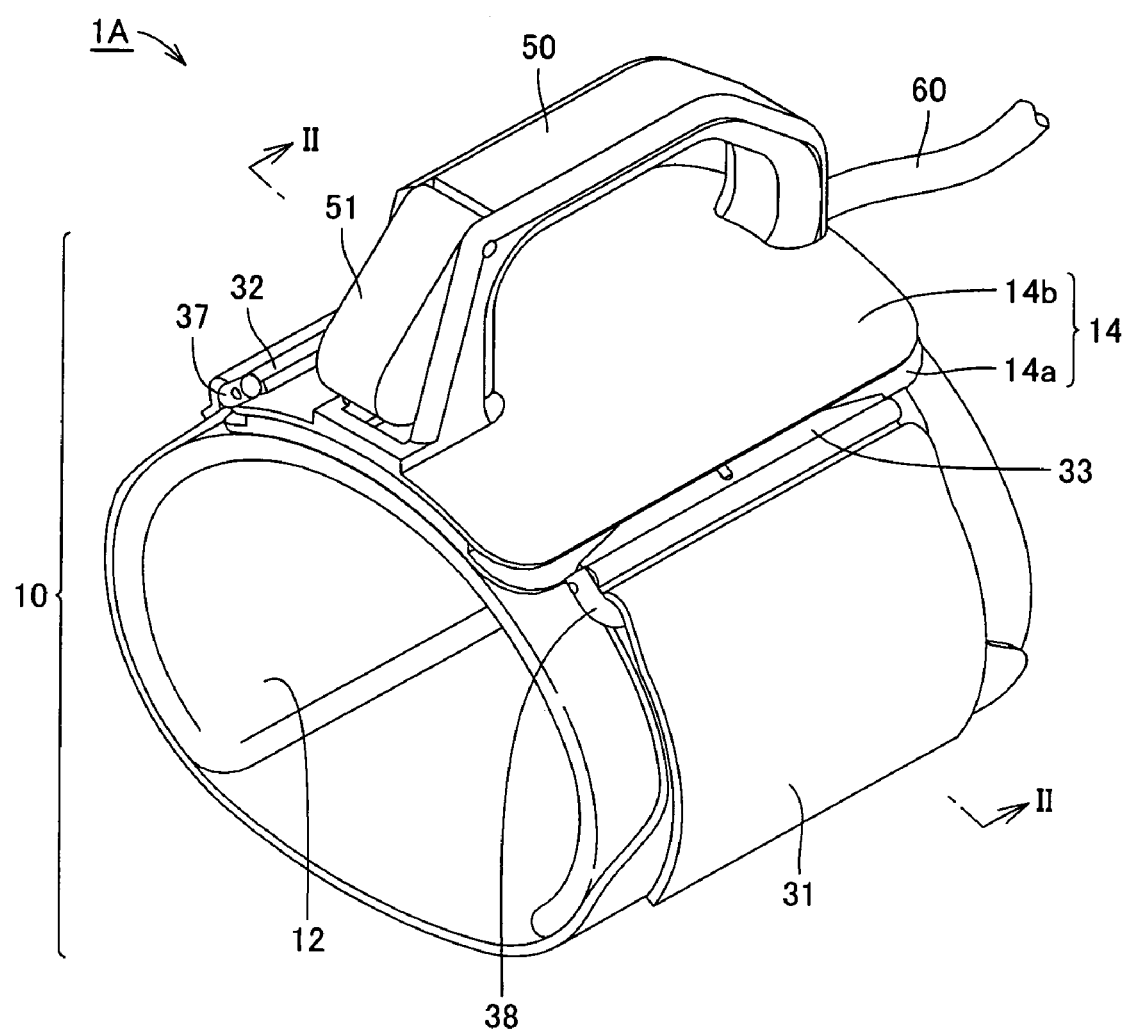
FIG. 1 is a perspective view of a cuff for a blood pressure monitor according to a first embodiment of the present invention.
Figure 2:
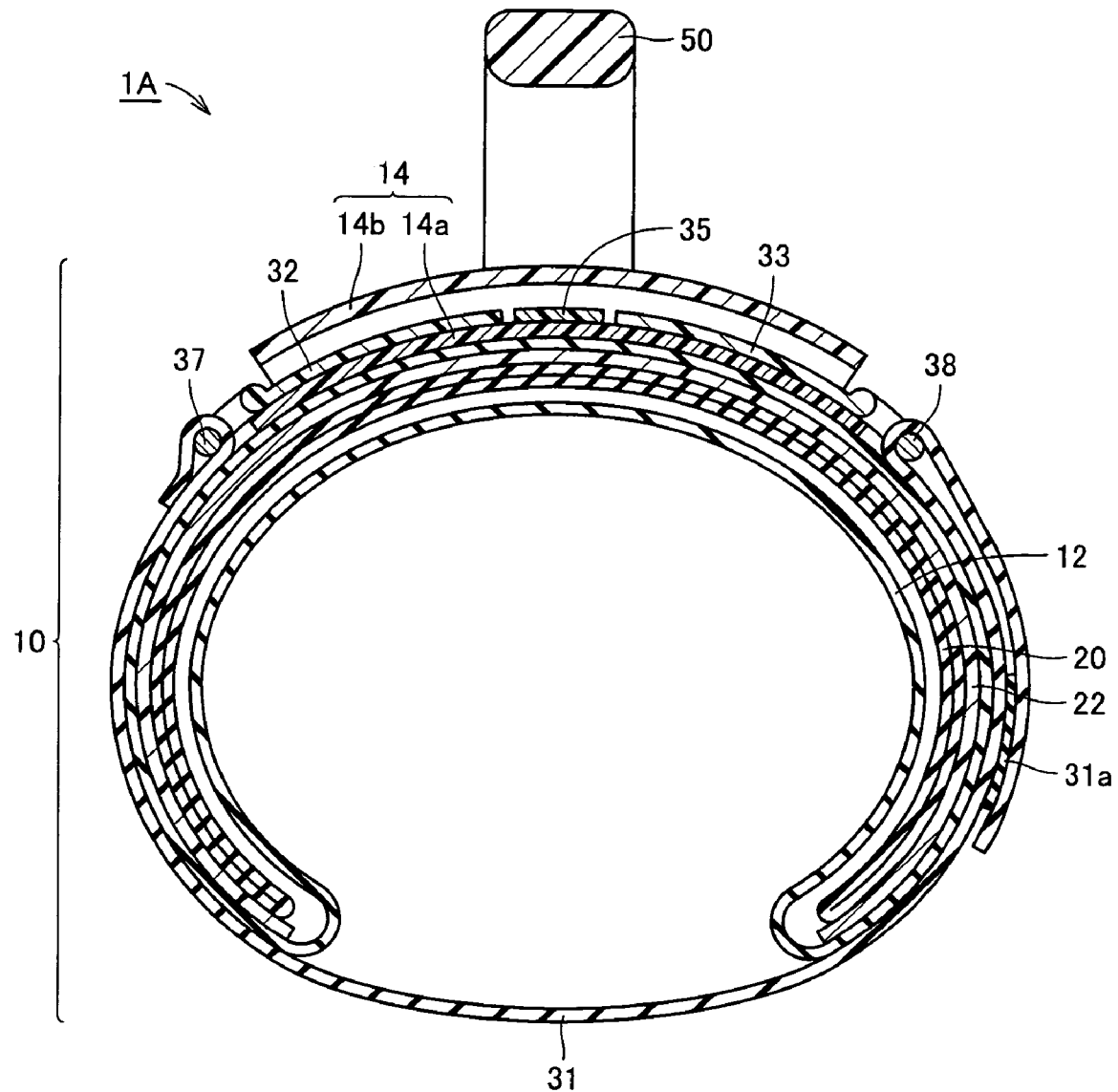
FIG. 2 is a schematic cross sectional view of the cuff for a blood pressure monitor shown in FIG. 1 taken along the line II—II therein.

FIG. 1 is a perspective view of a cuff for a blood pressure monitor according to a first embodiment of the present invention. FIG. 2 is a schematic cross sectional view of the cuff taken along the line II—II in FIG. 1. Firstly, an overall structure of the cuff for a blood pressure monitor of the present embodiment will be described with reference to FIGS. 1 and 2.

As shown in FIGS. 1 and 2, the cuff 1A for a blood pressure monitor according to the present embodiment includes a cuff main unit 10 wound around an upper arm identified as a measurement site so as to be fitted to the living body, and a handle 50 identified as a member that is provided on the outer peripheral surface of cuff main unit 10 and gripped by the hand when fitting the cuff. Cuff main unit 10 is formed in a cylindrical shape through which the upper arm can be inserted. Handle 50 is arranged to extend in a direction parallel to an axis line of cuff main unit 10 of the cylindrical shape, to protrude outward from an upper plate 14b of a base unit 14, which will be described later. As shown in FIG. 1, a push-button 51 is provided at a prescribed position of handle 50. Press-button 51 serves as a manipulation portion for switching an operation of a diameter increasing/decreasing mechanism, which will be described later.

As shown in FIG. 2, cuff main unit 10 includes, among others, an air bag 20 that is a fluid bag for pressing the measurement site of the living body, a curled elastic member 22 that is an elastic member wound annularly on the outside of air bag 20 and changeable in size in a radial direction, a cover member 12 for containing air bag 20 and curled elastic member 22 therein, a base unit 14 attached to the outside of cover member 12 extending in a circumferential direction, at an approximately central part of cover member 12 in its longitudinal direction, and a diameter increasing/decreasing mechanism for increasing or decreasing the diameter of curled elastic member 22 (details of which will be described later).

Air bag 20 is an inflatable, bag-shaped member, which may be formed, e.g., by laying two sheets of resin film one on another and bonding them together at their rims. The bore inside the air bag 20 is connected via a nipple (not shown) to a rubber tube 60 (see FIG. 1), which is in turn connected to a main unit of the blood pressure monitor (not shown). The bore of air bag 20 is increased and reduced in pressure by a pressurizing pump, a negative pressure pump and the like incorporated in the main unit of the blood pressure monitor upon measurement, for inflation/deflation of air bag 20.

Curled elastic member 22 is made of resin such as polypropylene, which is configured to retain its own annular shape, while being changeable in size in the radial direction. In the non-fitted state, curled elastic member 22 is maintained in the diameter-decreased state by a belt 31, which will be described later, while being biased in the radially outward direction. The above-described air bag 20 and curled elastic member 22 are contained in cover member 12 that is a low-friction member of cloth, for example.

Base unit 14 has a lower plate 14a fixed to an outer peripheral surface of cover member 12 or an outer peripheral surface of curled elastic member 22, and an upper plate 14b attached to lower plate 14a so as to cover an outer peripheral surface of lower plate 14a. A gap is provided inside base unit 14 between lower and upper plates 14a and 14b.

Figure 3A:
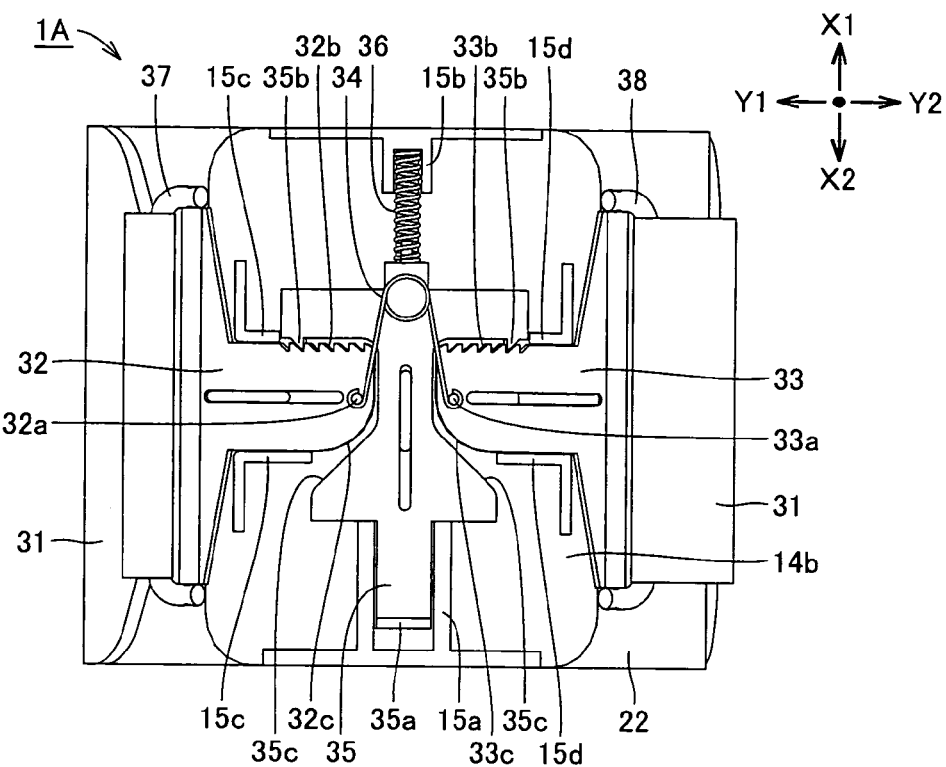
FIGS. 3A and 3B illustrate a configuration and an operation of a diameter increasing/decreasing mechanism of the cuff for a blood pressure monitor of the first embodiment, where
Figure 3B:
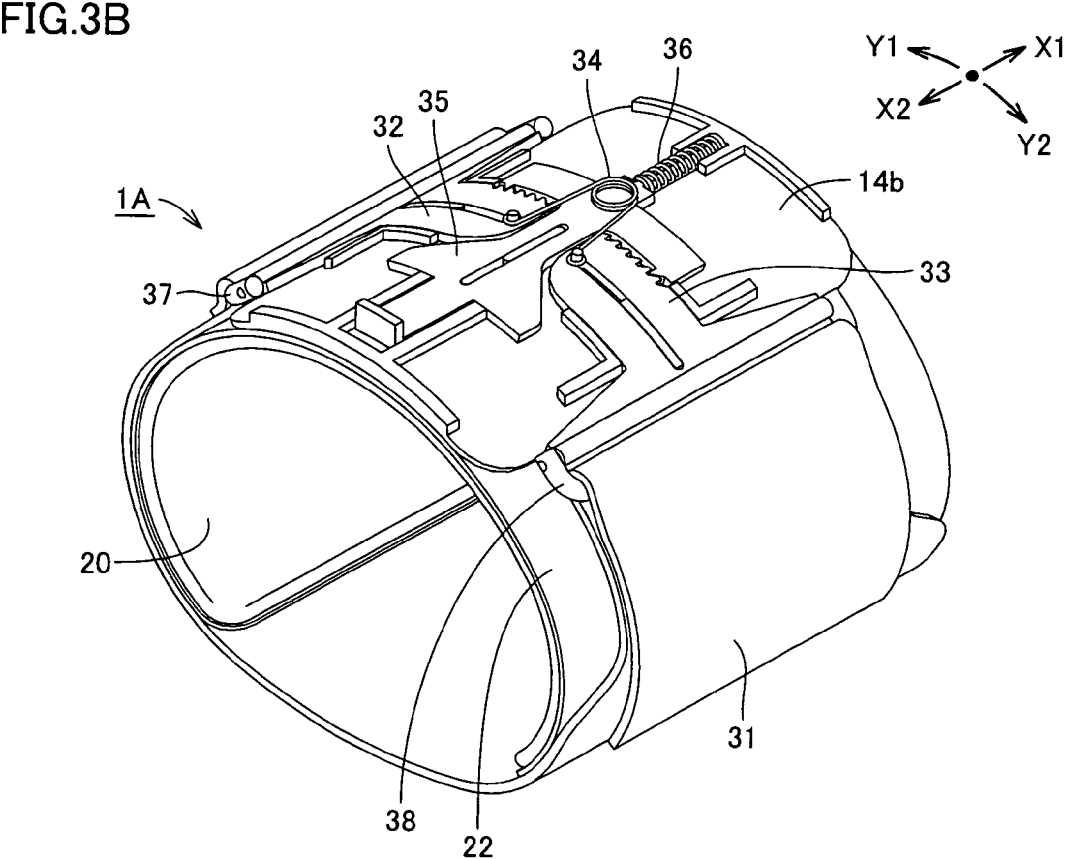
Figure 4A:
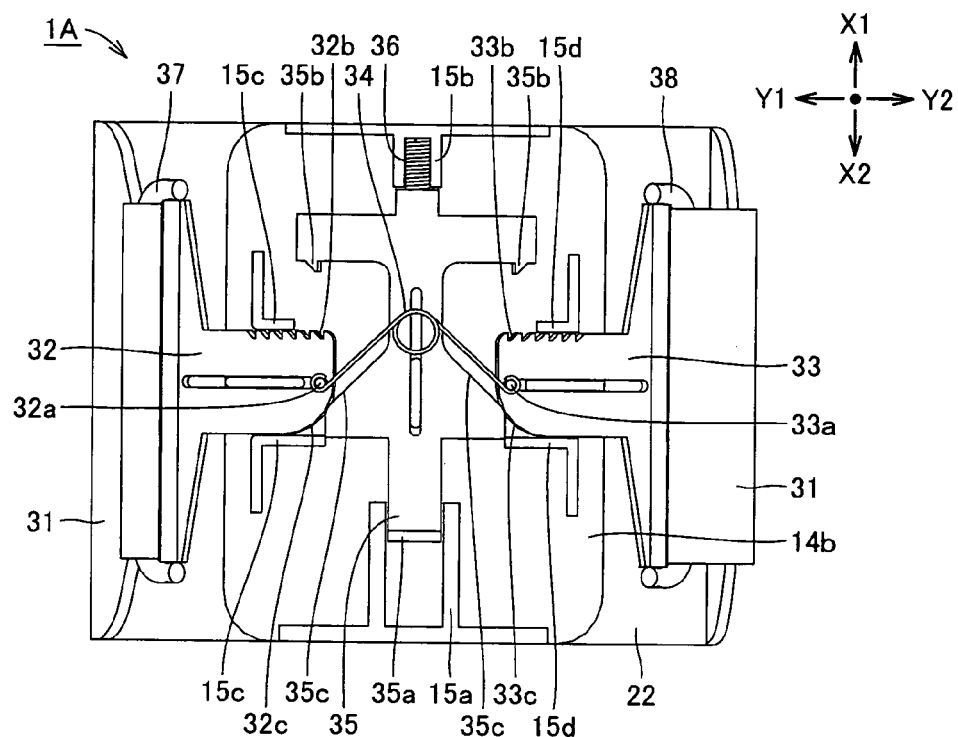
FIGS. 4A and 4B illustrate the configuration and the operation of the diameter increasing/decreasing mechanism of the cuff for a blood pressure monitor of the first embodiment, where
Figure 4B:
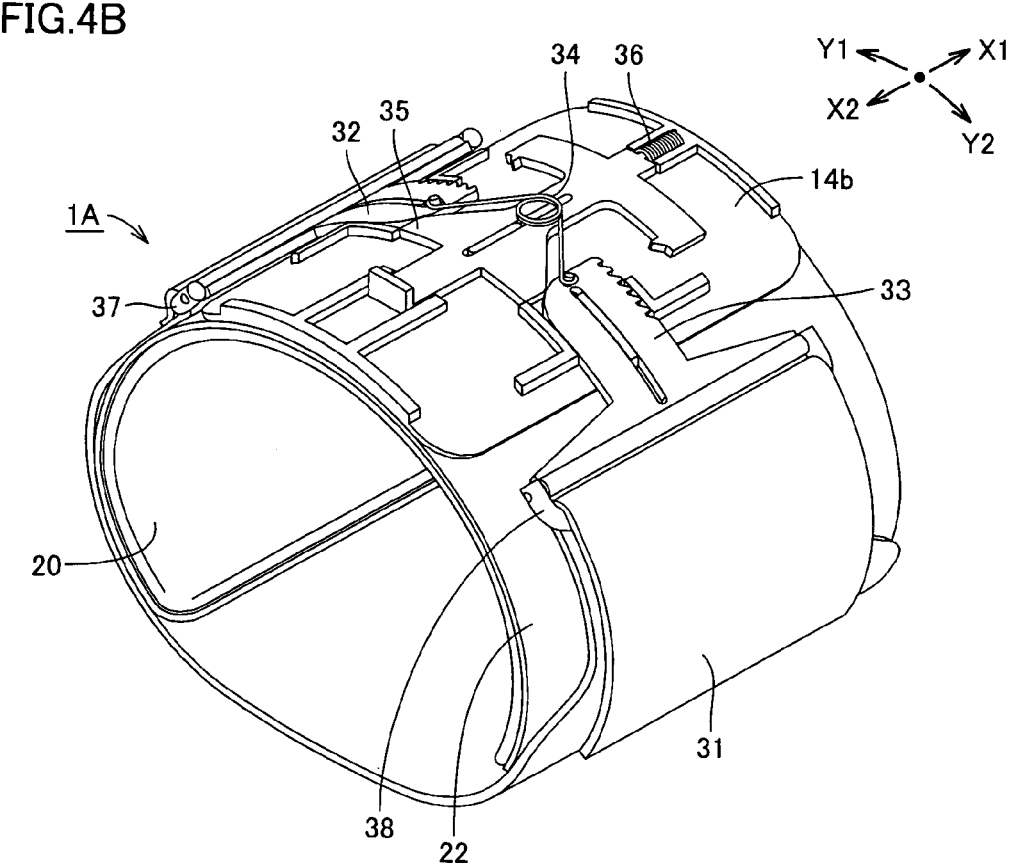

FIGS. 3A and 3B illustrate a configuration and an operation of a diameter increasing/decreasing mechanism of the cuff for a blood pressure monitor of the present embodiment. FIG. 3A shows in schematic top plan view and FIG. 3 shows in schematic perspective view the diameter increasing/decreasing mechanism in the non-fitted state. FIGS. 4A and 4B illustrate a diameter-increasing operation of the cuff for a blood pressure monitor of the present embodiment. FIG. 4A shows in schematic top plan view and FIG. 4B shows in schematic perspective view the diameter increasing/decreasing mechanism in the diameter-increased state. In FIGS. 3A, 3B, 4A and 4B, the above-described cover member 12, upper plate 14b of base unit 14, and handle 50 are not shown for the sake of simplicity.

Firstly, a configuration of the diameter increasing/decreasing mechanism of the cuff for a blood pressure member of the present embodiment will be described with reference to FIGS. 3A and 3B. As shown in FIGS. 3A and 3B, the diameter increasing/decreasing mechanism of the cuff 1A for a blood pressure monitor of the present embodiment includes a belt 31 that is a fastening band wound on the outside of curled elastic member 22, sliders 32, 33 constituting a pair of movable members that are attached to the respective ends in the circumferential direction of belt 31 via attachment rings 37, 38, respectively, and movable in the circumferential direction of cuff main unit 10, a first spring 34 that is an elastic body elastically connecting sliders 32 and 33, a slide lock 35 constituting a lock member that works in association with a push-button 51 provided at handle 50 to lock sliders 32, 33 in an immovable manner, and a second spring 36 that elastically biases slide lock 35 in one direction. Of these mechanical elements of the diameter increasing/decreasing mechanism, sliders 32, 33, first spring 34, slide lock 35, second spring 36 and others are arranged in the gap formed between lower plate 14a and upper plate 14b of base unit 14.

Belt 31 has its one end fixed to attachment ring 37, and the other end inserted through attachment ring 38 and folded back outwards. The folded part of belt 31 is secured to the unfolded part of belt 31 via a velcro fastener 31a (see FIG. 2), thereby enabling adjustment of the length of belt 31. Belt 31 is formed of a material that hardly stretches, and maintains curled elastic member 22 in the diameter-decreased state in opposition to the elastic force of curled elastic member 22 in the non-fitted state of the cuff.

Slide lock 35 is arranged on lower plate 14a of base unit 14, and has its moving direction restricted in the directions shown by arrows X1 and X2 in the figure, by means of a guide rib 15a formed on the main surface of lower plate 14a. On one end in the moving direction of slide lock 35, an abutment portion 35a is formed, which is configured to abut against push-button 51 of handle 50. Second spring 36, fitted in a rib 15b formed on the main surface of lower plate 14a, abuts against the other end in the moving direction of slide lock 35.

Sliders 32, 33 are arranged on the main surface of lower plate 14a of base unit 14, as is slide lock 35. Sliders 32, 33 have their moving directions restricted in the directions shown by arrows Y1 and Y2 in the figure, by means of guide ribs 15c, 15d formed on the main surface of lower plate 14a. Projections 32a, 33a are provided at the respective tip ends of sliders 32, 33, which are connected to each other by first spring 34. This achieves elastic connection between sliders 32 and 33.

Slide lock 35 has a pair of engagement projections 35b for engagement with engagement grooves 32b, 33b formed at sliders 32, 33, respectively, and a pair of tapered portions 35c for abutment against curved portions 32c, 33c formed at the tip ends of sliders 32, 33, respectively. Each of sliders 32, 33 is provided with a plurality of such engagement grooves 32b, 33b arranged in a row in the circumferential direction of cuff main unit 10.

Hereinafter, a diameter-increasing operation in cuff 1A for a blood pressure monitor of the present embodiment will be described with reference to FIGS. 3A, 3B, 4A and 4B. In the non-fitted state of cuff 1A for a blood pressure monitor, push-button 51 provided at handle 50 is not depressed by a subject, and slide lock 35 is in the position shown in FIGS. 3A and 3B, being biased by second spring 36 in the direction shown by arrow X2 in the figure. In this state, the pair of engagement projections 35b provided at slide lock 35 are in engagement with engagement grooves 32b, 33b of sliders 32, 33, respectively, thereby locking sliders 32, 33 in an immovable manner.

In this state, when the subject grips handle 50 and depresses push-button 51 so as to fit cuff 1A for a blood pressure monitor on the measurement site of the upper arm, push-button 51 comes to abut against abutment portion 35a of slide lock 35, thereby pushing slide block 35 backwards. In response, slide lock 35 moves in the direction shown by arrow X1 in the figure in opposition to the bias force of second spring 36. The engagement between each of engagement projections 35b of slide lock 35 and corresponding engagement grooves 32b, 33b of sliders 32, 33 is released, and tapered portions 35c of slide lock 35 come to abut against curved portions 32c, 33c of sliders 32, 33, respectively, thereby pushing sliders 32, 33 backwards. As a result, sliders 32, 33 move in the directions increasing the distance therebetween, in opposition to the bias force of first spring 34 (i.e., slider 32 moves in the direction shown by arrow Y1 and slider 33 moves in the direction shown by arrow Y2 in the figure).

With the diameter-increasing operation described above, belt 31 attached to sliders 32, 33 via attachment rings 37, 38 loosens to increase its length in the circumferential direction of cuff main unit 10. As such, curled elastic member 22 is increased in diameter by its own elastic force acting in the radially outward direction, and the cross-sectional area of the hollow portion of cuff main unit 10 increases. This diameter-increased state of curled elastic member 22 released from the diameter-decreased state is maintained as long as the subject continues depressing push-button 51.

Figure 5:
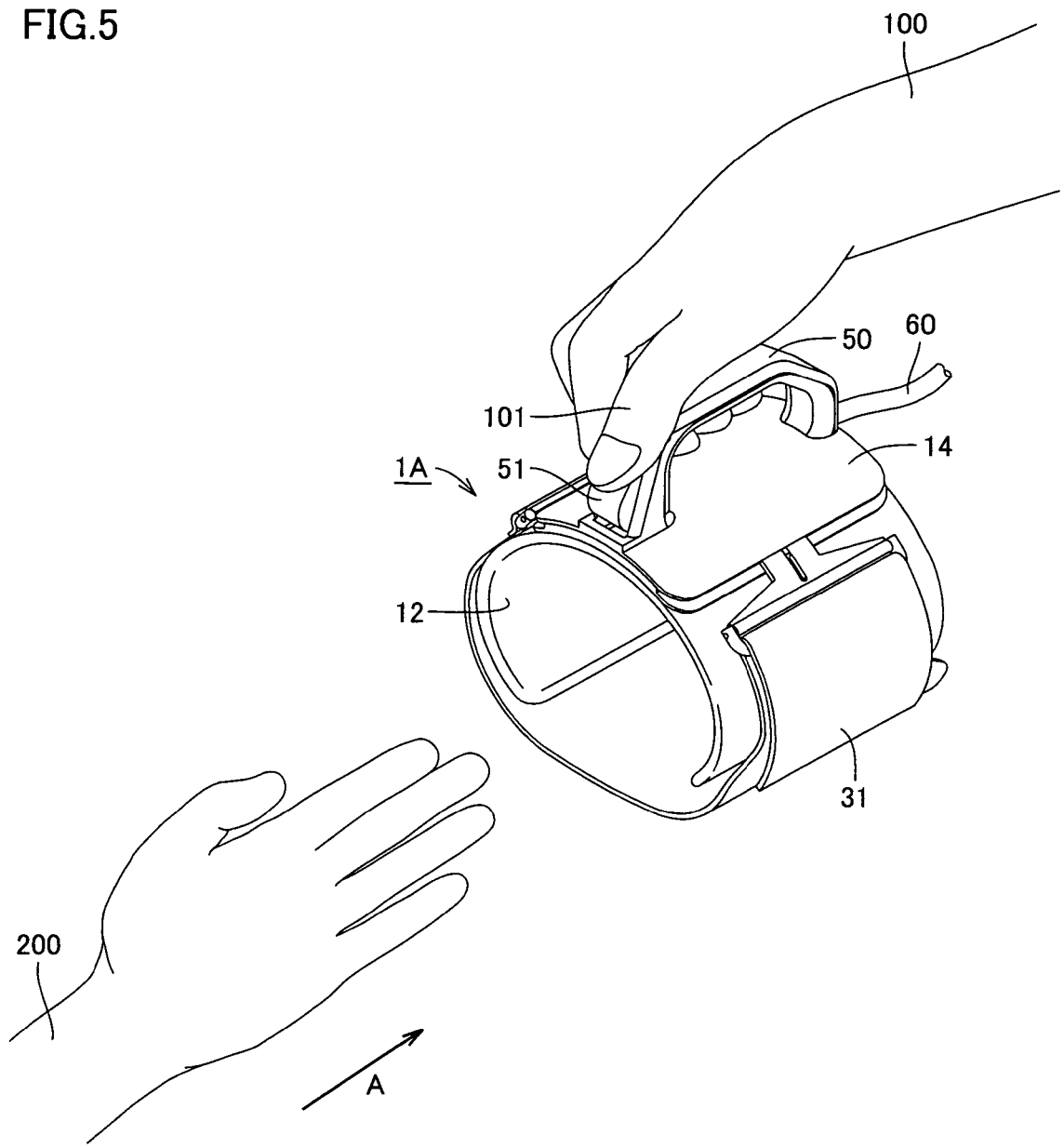
FIG. 5 is a schematic diagram illustrating how the cuff for a blood pressure monitor of the first embodiment is fitted to an upper arm.

FIG. 5 schematically illustrates how the cuff for a blood pressure monitor of the first embodiment is fitted to the upper arm. As shown in FIG. 5, in the state where the subject is gripping handle 50 with the right hand 100 and depressing push-button 51 on handle 50 with the thumb 101 of the right hand 100, curled elastic member 22 is in the diameter-increased state with the hollow portion of cuff main unit 10 increased in size, as described above. In this state, the subject inserts the other hand not engaged in manipulation, i.e., the left hand 200, through the hollow portion of cuff main unit 10 in the direction shown by an arrow A in the figure. Then, the subject places cuff main unit 10 at a prescribed position of the left upper arm, and leaves thumb 101 of the right hand 100 from push-button 51 to release the depression thereof.

Figure 6A:
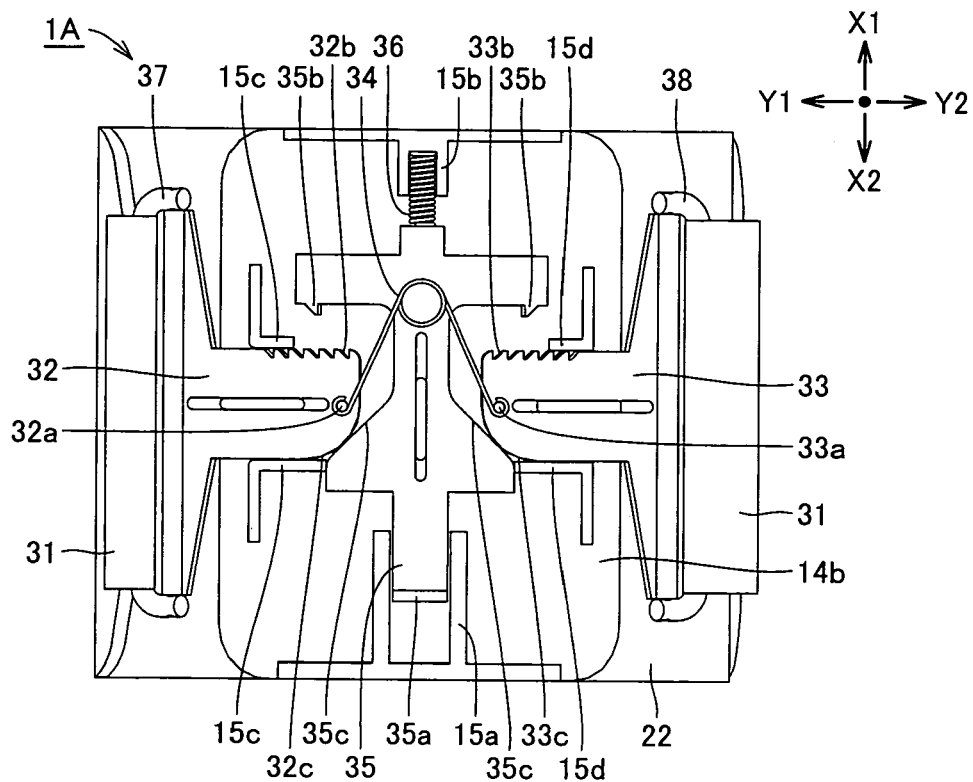
FIGS. 6A and 6B illustrate a diameter-decreasing operation of the diameter increasing/decreasing mechanism of the cuff for a blood pressure monitor of the first embodiment when a push-button is released, where
Figure 6B:
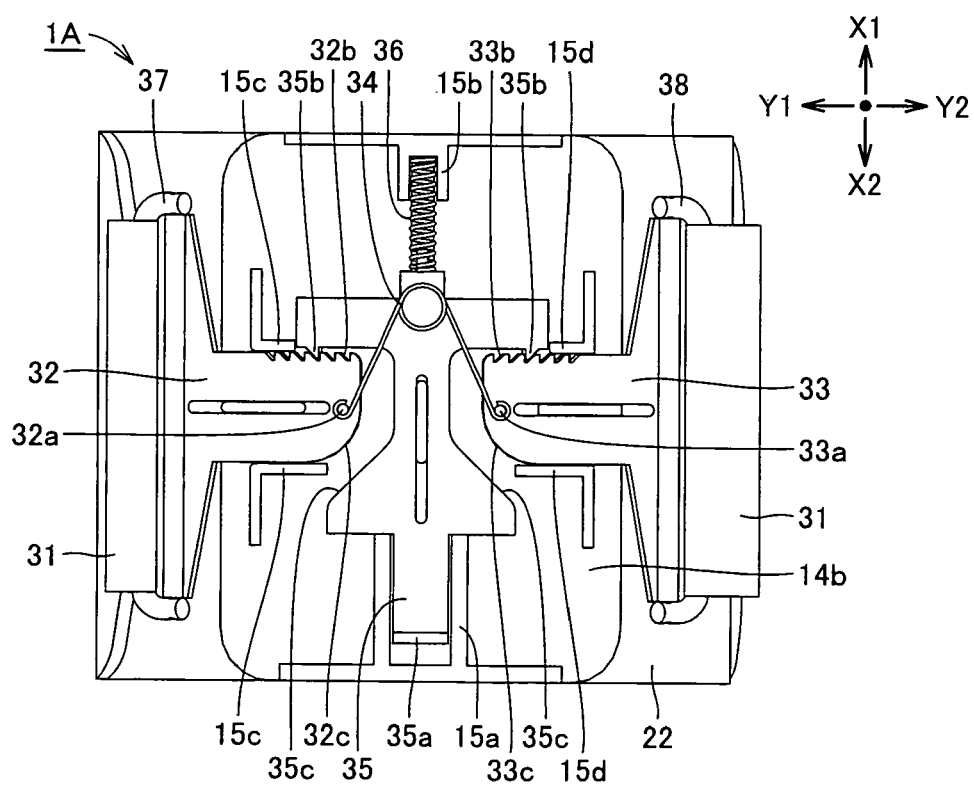

FIGS. 6A and 6B illustrate a diameter-decreasing operation of the diameter increasing/decreasing mechanism of the cuff for a blood pressure monitor of the present embodiment, when releasing the depression of the push-button as described above. FIG. 6A shows in schematic top plan view the mechanism in the course of the diameter-decreasing operation, and FIG. 6B shows in schematic top plan view the mechanism after completion of the diameter-decreasing operation. The diameter-decreasing operation of the diameter increasing/decreasing mechanism of the present embodiment will now be described with reference to FIGS. 6A and 6B.

As shown in FIG. 6A, when the subject releases the depression of push-button 51 so as to fit cuff 1A for a blood pressure monitor on the measurement site of the upper arm, abutment of push-button 51 against abutment portion 35a of slide lock 35 is released, and slide lock 35 begins to move in the direction shown by arrow X2 in the figure by the elastic force of second spring 36. At this time, abutment of tapered portions 35c of slide lock 35 against corresponding curved portions 32c, 33c of sliders 32, 33 is also released, so that sliders 32, 33 begin to move in the directions approaching each other (i.e., slider 32 in the Y2 direction and slider 33 in the Y1 direction) by the elastic force of first spring 34.

With the movement of sliders 32, 33, the ends of belt 31 attached to sliders 32, 33 via attachment rings 37, 38 are pulled toward each other, and correspondingly, belt 31 reduces the diameter of curled elastic member 22 in opposition to the elastic force of curled elastic member 22, thereby decreasing the cross-sectional area of the hollow portion of cuff main unit 10. The measurement site of the upper arm, however, is present in the hollow portion of cuff main unit 10, which prevents reduction in diameter of curled elastic member 22 beyond a prescribed extent. This stops further fastening of belt 31 and hence further movement of attachment rings 37, 38.

Meanwhile, as shown in FIG. 6B, slide lock 35 continues to move by means of second spring 36, until it abuts against guide rib 15a provided at lower plate 14a of base unit 14. At this time, the pair of engagement projections 35b of slide lock 35 come into engagement with prescribed ones of the plurality of engagement grooves 32b, 33b arranged in rows on sliders 32, 33, respectively, so that sliders 32, 33 are locked by slide lock 35, with further movement prohibited. As a result, the fastening force of belt 31 against the upper arm is maintained at a constant level, allowing air bag 20 to be pressed against the upper arm with an appropriate pressing force by curled elastic member 22.

Figure 7:
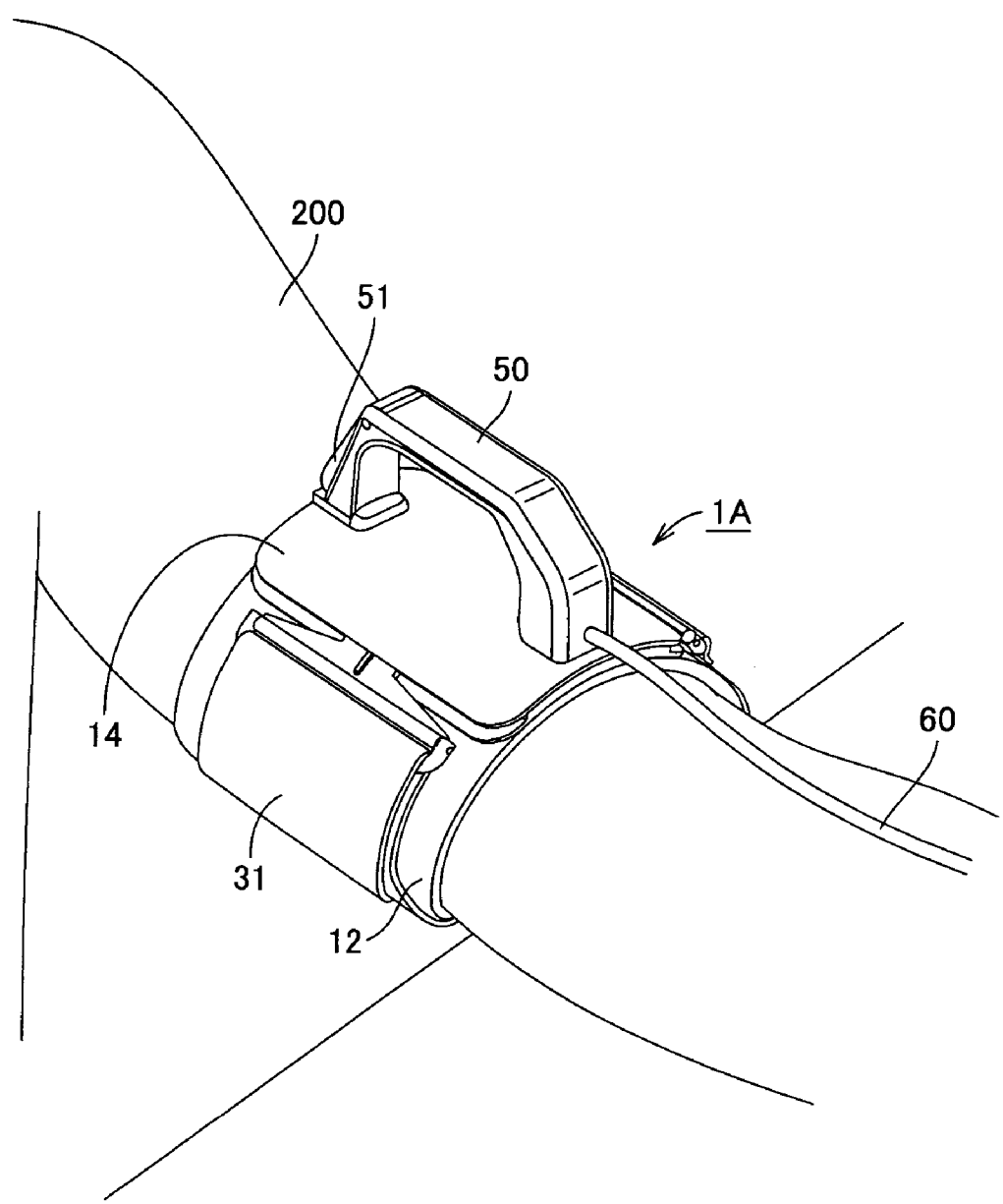
FIG. 7 is a perspective view showing the state where the cuff for a blood pressure monitor of the first embodiment is fitted to an upper arm.

FIG. 7 is a perspective view showing the state where the cuff for a blood pressure monitor of the present embodiment is fitted to the upper arm. With the series of manipulations by the subject described above, the diameter increasing/decreasing mechanism incorporated in cuff main unit 10 operates in the above-described manner, whereby cuff main unit 10 is fitted to the upper arm of the subject with an appropriate fastening force, as shown in FIG. 7. As the pressurized air is delivered in this state from the main unit of the blood pressure monitor via rubber tube 60 to air bag 20, air bag 20 is tightened around the upper arm to thereby press the artery located inside the upper arm, thus enabling measurement of the blood pressure values.

In the above-described cuff 1A for a blood pressure monitor according to the present embodiment, the mechanical elements of the diameter increasing/decreasing mechanism, such as belt 31, sliders 32, 33, first spring 34, slide lock 35, second spring 36, attachment rings 37, 38 and others, work in cooperation with each other to increase/decrease the diameter of curled elastic member 22 that is the elastic member, or maintain curled elastic member 22 in the diameter-decreased state. That is, some or all of the mechanical elements constituting the diameter increasing/decreasing mechanism function as the diameter-decreased state maintaining mechanism that maintains curled elastic member 22 in the diameter-decreased state, the diameter-decreased state releasing mechanism that releases curled elastic member 22 to the diameter-increased state, and the diameter-forcibly-decreasing mechanism that forcibly decreases the diameter of curled elastic member 22 in the diameter-increased state. The mechanical elements implementing the diameter-decreased state maintaining mechanism, the diameter-decreased state releasing mechanism, and the diameter-forcibly-decreasing mechanism work in association with manipulation of push-button 51 that is the manipulation portion provided at handle 50.

In the above-described cuff 1A for a blood pressure monitor of the present embodiment, push-button 51 serving as the manipulation portion for switching the operation of the diameter increasing/decreasing mechanism is provided at handle 50 that is the member held by the hand when fitting the cuff. This permits gripping of handle 50 and depressing of push-button 51 to be carried out simultaneously with the hand other than the hand to which cuff main unit 10 is to be fitted. Accordingly, it is possible to fit cuff 1A for a blood pressure monitor on the measurement site of the upper arm in one step with a single hand, which ensures outstanding ease of handling upon fitting. As a result, the fitting operation becomes easy even for elderly people and women relatively weak in physical strength. Further, since the fitting operation is easy, it is relatively easy to mount cuff main unit 10 at an appropriate position on the upper arm, which reduces occurrence of measurement errors due to displacement of the fitted position, thereby enabling accurate measurement of the blood pressure values. Still further, since curled elastic member 22 presses air bag 20 against the upper arm with an appropriate pressing force, accurate measurement of the blood pressure values can be realized repeatedly. Accordingly, cuff 1A for a blood pressure monitor having the above-described configuration can implement a cuff for a blood pressure monitor that can readily be fitted and ensures accurate and stable measurement of blood pressure values.

Further, in cuff 1A for a blood pressure monitor of the present embodiment, handle 50 is preferably arranged on the outer peripheral surface of cuff main unit 10 at a location corresponding to the position of the artery inside the upper arm around which cuff main unit 10 is wound. With this configuration, the handle can serve as an indicator for accurate positioning of cuff main unit 10, thereby facilitating fitting of the cuff to the appropriate position.

Furthermore, in cuff 1A for a blood pressure monitor of the present embodiment, in the state where cuff main unit 10 is fitted on the upper arm, handle 50 may be gripped with the right hand 100 and push-button 51 may be depressed with the thumb 101 of the right hand 100 to increase the diameter of curled elastic member 22, to dismount cuff main unit 10 from the left hand 200, and then depression of push-button 51 may be released. This permits dismounting of cuff 1A for a blood pressure monitor from the measurement site of the upper arm in one step. As such, great ease of handling is ensured not only for mounting but also for dismounting of the cuff.

Although the push-button has been explained as an example of the manipulation portion in cuff 1A for a blood pressure monitor of the first embodiment, the manipulation portion may be a slide button, a dial button, or a lever as will be explained in the second embodiment below. Further, although the case of arranging the push-button serving as the manipulation portion at the handle in a position enabling manipulation thereof with the thumb has been explained in the first embodiment, the position for arrangement of the manipulation portion is not restricted thereto. The manipulation portion may be arranged at any position of the handle. Further, the position for arrangement of the manipulation portion is not restricted to the position on the handle, but it may be arranged on the cuff main unit in the vicinity of the handle. All that is needed is that the manipulation portion is arranged at a position that enables manipulation thereof with the very hand holding the handle.

Further, the configuration of the diameter increasing/decreasing mechanism is not restricted to the one explained above. The diameter increasing/decreasing mechanism of any configuration may be employed, as long as the diameter of the curled elastic member that is the elastic member can be increased or decreased in association with the manipulation of the manipulation portion.

Furthermore, each of the diameter-increasing operation and the diameter-decreasing operation does not necessarily have to be done in association with a single manipulation (of depression of the push-button, and of release thereof). For example, the diameter-increasing operation may be done with manipulation of the first time, and the diameter-decreasing operation may be done with manipulation of the second time. It is also possible to configure the diameter-increasing operation and the diameter-decreasing operation to be achieved in association with depression of separate push-buttons.

SECOND EMBODIMENT

Figure 8:
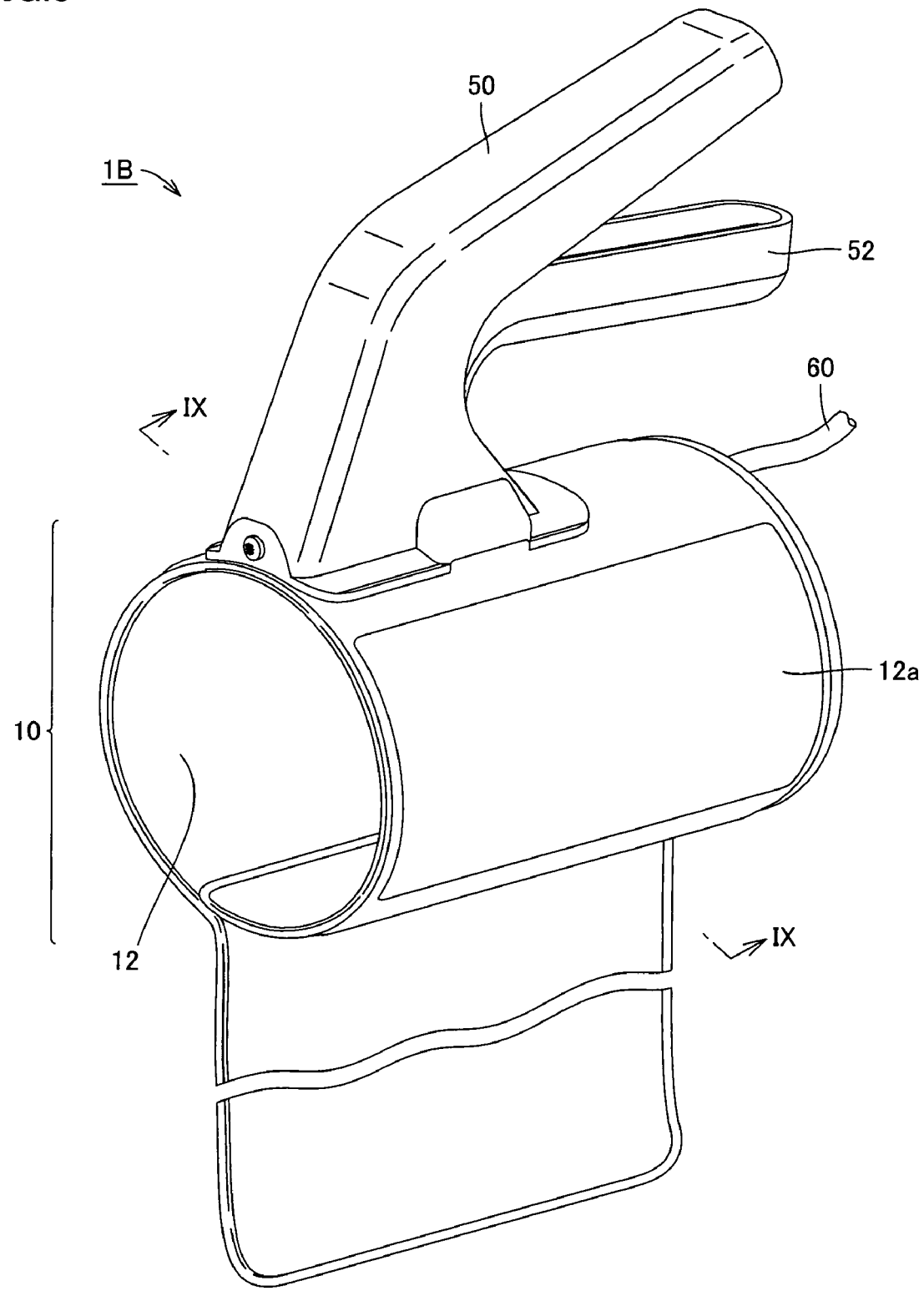
FIG. 8 is a perspective view of a cuff for a blood pressure monitor according to a second embodiment of the present invention.
Figure 9:
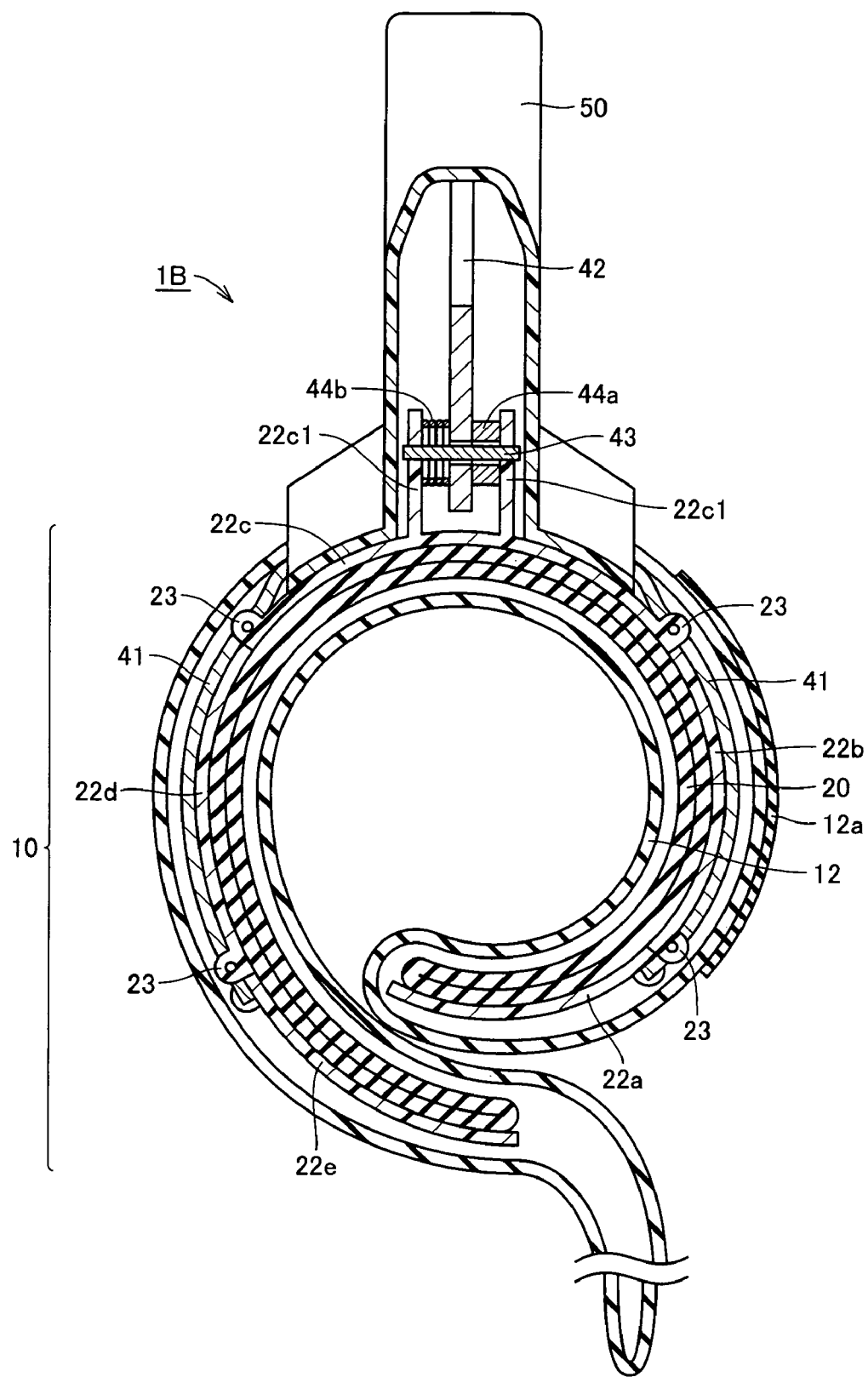
FIG. 9 is a schematic cross sectional view of the cuff for a blood pressure monitor shown in FIG. 8, taken along the line IX—IX therein.

FIG. 8 is a perspective view of a cuff for a blood pressure monitor according to a second embodiment of the present invention. FIG. 9 is a schematic cross sectional view of the cuff taken along the line IX—IX in FIG. 8. Firstly, an overall structure of the cuff for a blood pressure monitor of the present embodiment will be described with reference to FIGS. 8 and 9.

As shown in FIGS. 8 and 9, a cuff 1B for a blood pressure monitor of the present embodiment includes a cuff main unit 10 wound around an upper arm that is a measurement site to be fitted to the living body, and a handle 50 provided on the outer peripheral surface of cuff main unit 10 and gripped by the hand when mounting the cuff. Cuff main unit 10 is formed in a cylindrical shape to receive the upper arm therein, which has a slit-like opening at a prescribed position in the circumferential direction for inserting the upper arm therethrough. Handle 50 is provided to extend parallel to the axis line of cuff main unit 10 of the cylindrical shape, to protrude outward from one (i.e., segment 22c) of segments 22a–2e constituting a curled elastic member 22, which will be described later, that is located at the center in the circumferential direction. As shown in FIG. 8, a lever 52 is provided at a prescribed position of handle 50. Lever 52 serves as the manipulation portion for switching the operation of a diameter increasing/decreasing mechanism, which will be described later.

As shown in FIG. 9, cuff main unit 10 includes, among others, an air bag 20 that is a fluid bag for pressing the measurement site of the living body, a curled elastic member 22 that is an elastic member wound annularly on the outside of air bag 20 and changeable in size in a radial direction, a cover member 12 for containing air bag 20 and curled elastic member 22 therein, and a diameter increasing/decreasing mechanism for increasing or decreasing the diameter of curled elastic member 22.

Air bag 20 is an inflatable, bag-shaped member, which may be formed, e.g., by laying two sheets of resin film one on another and bonding them together at their rims. The bore inside air bag 20 is connected via a nipple (not shown) to a rubber tube 60 (see FIG. 8), which is in turn connected to a main unit of the blood pressure monitor (not shown). The bore of air bag 20 is increased and reduced in pressure by a pressurizing pump, a negative pressure pump and the like incorporated in the main unit of the blood pressure monitor upon measurement, for inflation/deflation of air bag 20.

Curled elastic member 22 consists of a plurality of segments formed of resin members such as polypropylene or metal plates, and hinges and elastic bodies connecting the segments, and is configured to retain its annular shape and to be radially changeable in size. More specifically, curled elastic member 22 of cuff 1B for a blood pressure monitor of the present embodiment includes five segments 22a–22e arranged along the circumferential direction, hinges 23 (see FIG. 10) each connecting neighboring ones of segments 22a–22e, and connection springs 24 (see FIG. 10) that are the elastic bodies each connecting neighboring ones of segments 22a–22e. The above-described air bag 20 and curled elastic member 22 are contained in a cover member 12 formed of a low-friction member of cloth, for example, as described above. Cover member 12 has an extension portion on its one end in the circumferential direction opposite to the end having a velcro fastener 12a provided on the outer peripheral surface, such that the both ends overlap with each other in the fitted state of the cuff.

The diameter increasing/decreasing mechanism includes, among others, a wire 41 that is a line-shaped or band-shaped member extending along the outside of curled elastic member 22, and a pivoting member 42 serving as a pull-up mechanism that pulls up wire 41 at its approximately central part, in the direction coming apart from the outer surface of curled elastic member 22. Pivoting member 42 is a hook-shaped member that is arranged inside the handle 50 (see FIGS. 12A and 12B). The part of pivoting member 42 corresponding to its handle or grip portion operates integrally with the above-described lever 52. Pivoting member 42 is attached, in a pivotable manner, to a support shaft 43 that is inserted through a pair of support portions 22c1 arranged erected on the outer peripheral surface of segment 22c that is located at the center in the circumferential direction of curled elastic member 22. Pivoting member 42 is sandwiched between a spacer 44a and a return spring 44b that are also inserted through support shaft 43. Return spring 44b serves as a member that biases pivoting member 42 in a prescribed rotative direction, when pivoting member 42 supported by support shaft 43 in a pivotable manner turns in a prescribed direction, to make it return to its original position. A pull-up portion 42a1 is provided at one end of pivoting member 42 on the opposite side from the grip portion with respect to the center of rotation of pivoting member 42 at support shaft 43.

A notch 42a2 is provided at pull-up portion 42a1, in a prescribed position at the upper part thereof. This notch 42a2 catches the above-described wire 41 (see FIGS. 12A and 12B). Wire 41 is preferably formed of a member that hardly stretches even when its ends are pulled in the opposite directions. For example, it is formed of a metal material or a resin material having a small modulus of elasticity. Wire 41 has its ends fixed to securing members 22a1 and 22e1 that are provided at segments 22a and 22e, respectively, located at the respective ends in the circumferential direction of curled elastic member 22. Wire 41 is inserted through a guide portion 45 provided on the outer peripheral surface of segment 22c.

Figure 10:
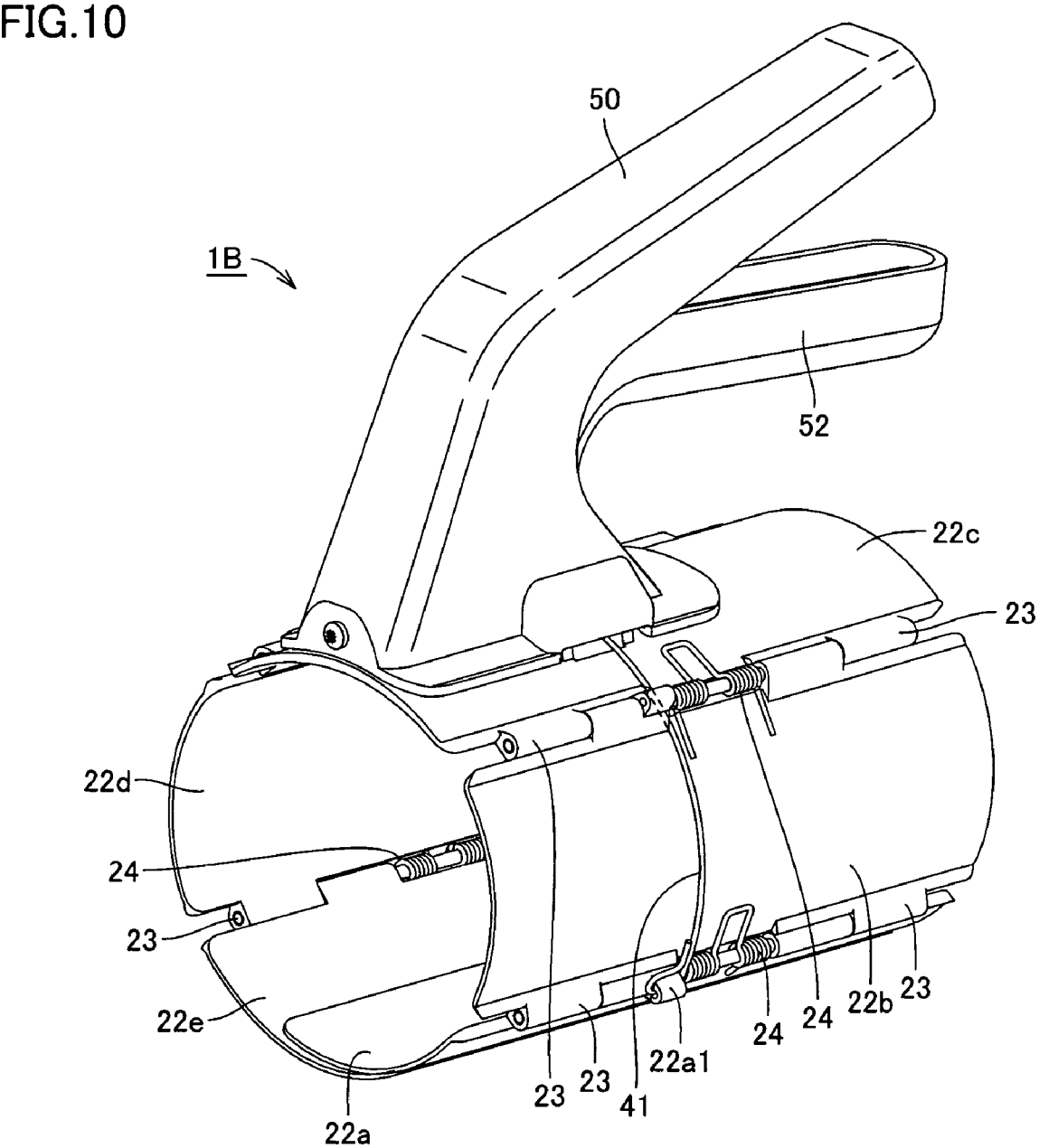
FIGS. 10 and 11 illustrate a configuration and a diameter-increasing operation of a diameter increasing/decreasing mechanism of the cuff for a blood pressure monitor of the second embodiment.
Figure 11:
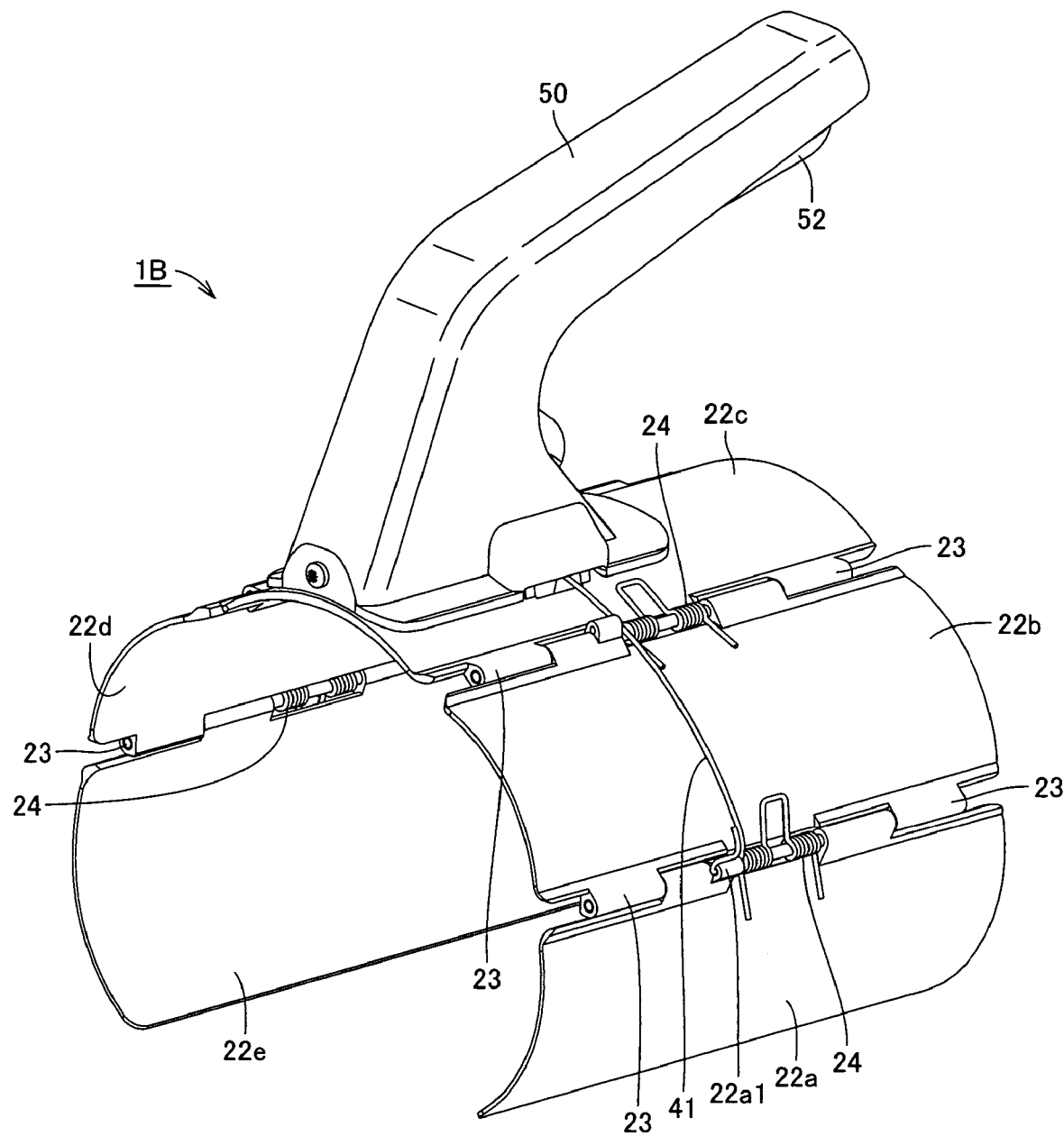
Figure 12A:
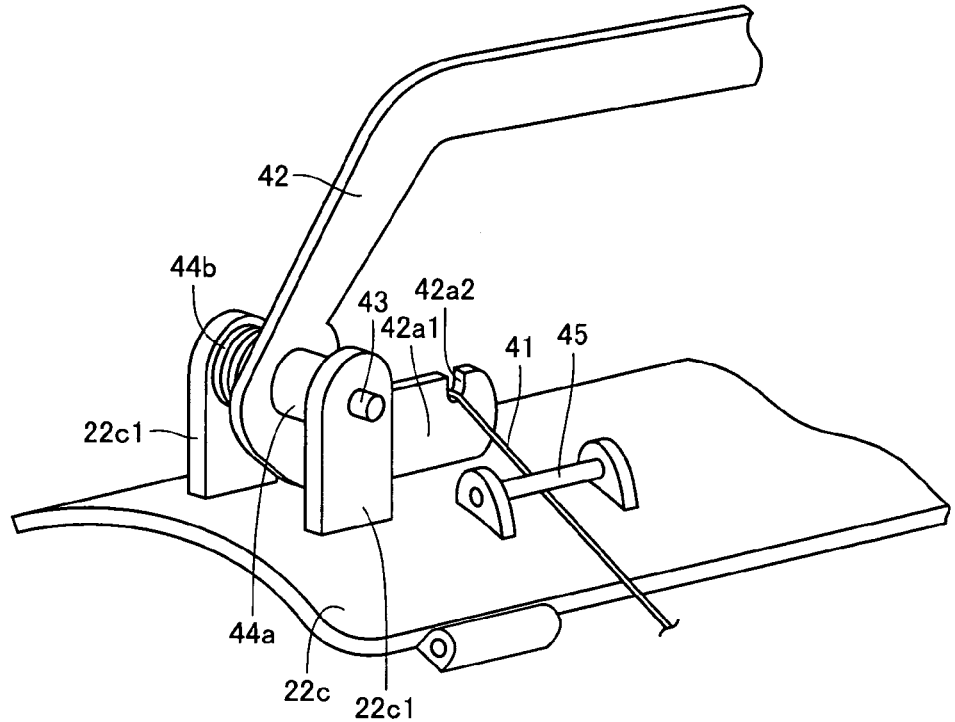
FIGS. 12A and 12B are schematic perspective views showing an internal structure of a handle of the cuff for a blood pressure monitor of the second embodiment as well as a main part of the diameter increasing/decreasing mechanism working in association with a lever, where
Figure 12B:
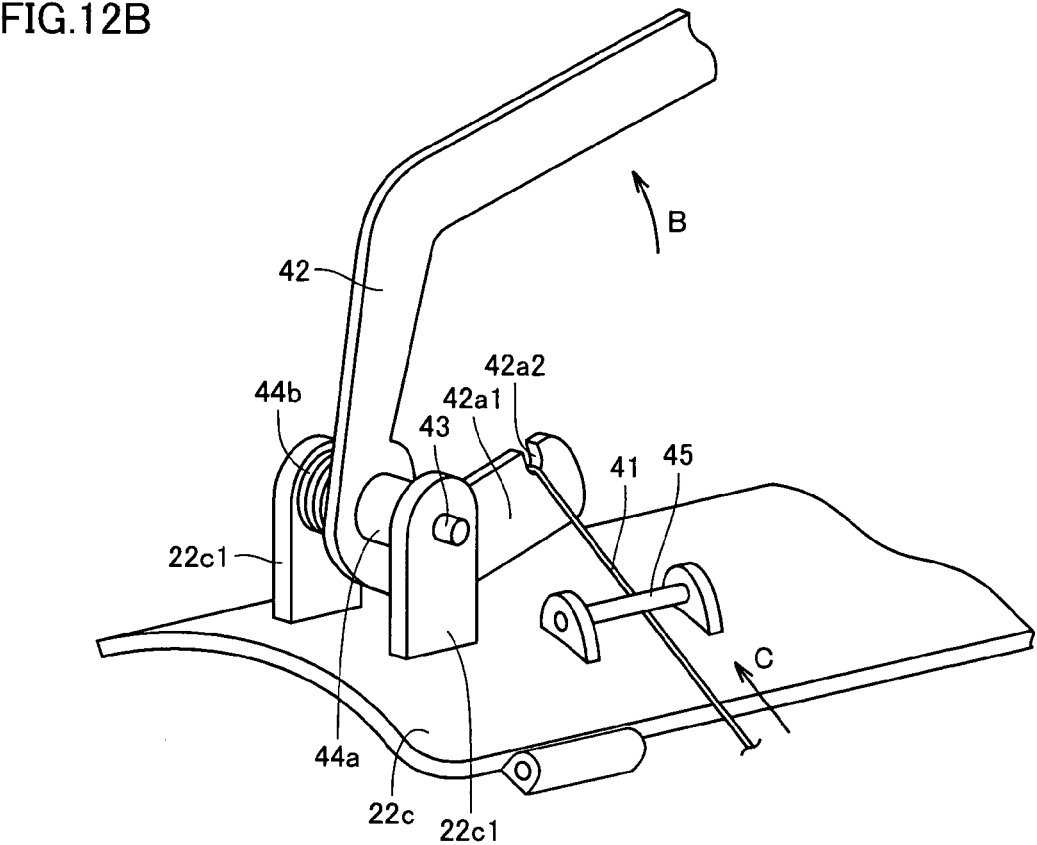

FIGS. 10 and 11 illustrate a configuration and a diameter-increasing operation of the diameter increasing/decreasing mechanism of the cuff for a blood pressure monitor of the present embodiment. FIGS. 12A and 12B are schematic perspective views showing the internal structure of the handle of the cuff for a blood pressure monitor of the present embodiment and a main part of the diameter increasing/decreasing mechanism that works in cooperation with the lever. FIG. 12A shows the state where the lever is not operated, and FIG. 12B shows the state where the lever is operated. Hereinafter, the diameter-increasing operation of the cuff for a blood pressure monitor of the present embodiment will be described with reference to FIGS. 10, 11, 12A and 12B. In these figures, the above-described cover member 12 and air bag 20 are not shown for the sake of simplicity.

As shown in FIG. 10, in the non-fitted state of cuff 1B for a blood pressure monitor, lever 52 provided at handle 50 is not manipulated by the subject. Thus, wire 41 arranged along the outside of curled elastic member 22 is not intentionally pulled up by pivoting member 42 identified as the pull-up mechanism (see FIG. 12A). Curled elastic member 22 is not intentionally subjected to external force, and remains in a diameter-decreased state.

In this state, when the subject grips handle 50 and manipulates lever 52 so as to fit cuff 1B for a blood pressure monitor on the measurement site of the upper arm, as shown in FIG. 12B, the grip portion of pivoting member 42 arranged in the vicinity of handle 50 is pulled up in the direction shown by an arrow B in the figure, causing pivoting member 42 to turn around support shaft 43. Correspondingly, pull-up portion 42a1 of pivoting member 42 turns in the direction shown by arrow B in the figure, causing the approximately central part of wire 41 to be pulled up to increase its distance from the outer surface of segment 22c, and accordingly, the both ends of wire 41 are pulled up in the direction shown by an arrow C in the figure. With wire 41 pulled up, segments 22a, 22e secured to the respective ends of wire 41 are spread in the radially outward direction in opposition to the elastic force of respective connection springs 24, which is accompanied by spreading of segments 22b and 22d in the radially outward direction. In this manner, segments 22a, 22b, 22d and 22e of curled elastic member 22 are spread in the radially outward direction to increase the diameter of curled elastic member 22, and thus, the cross sectional area of the hollow portion of cuff main unit 10 increases. This diameter-increased state of curled elastic member 22 released from the diameter-decreased state is maintained as long as the subject keeps the manipulated state of lever 52.

Figure 13:
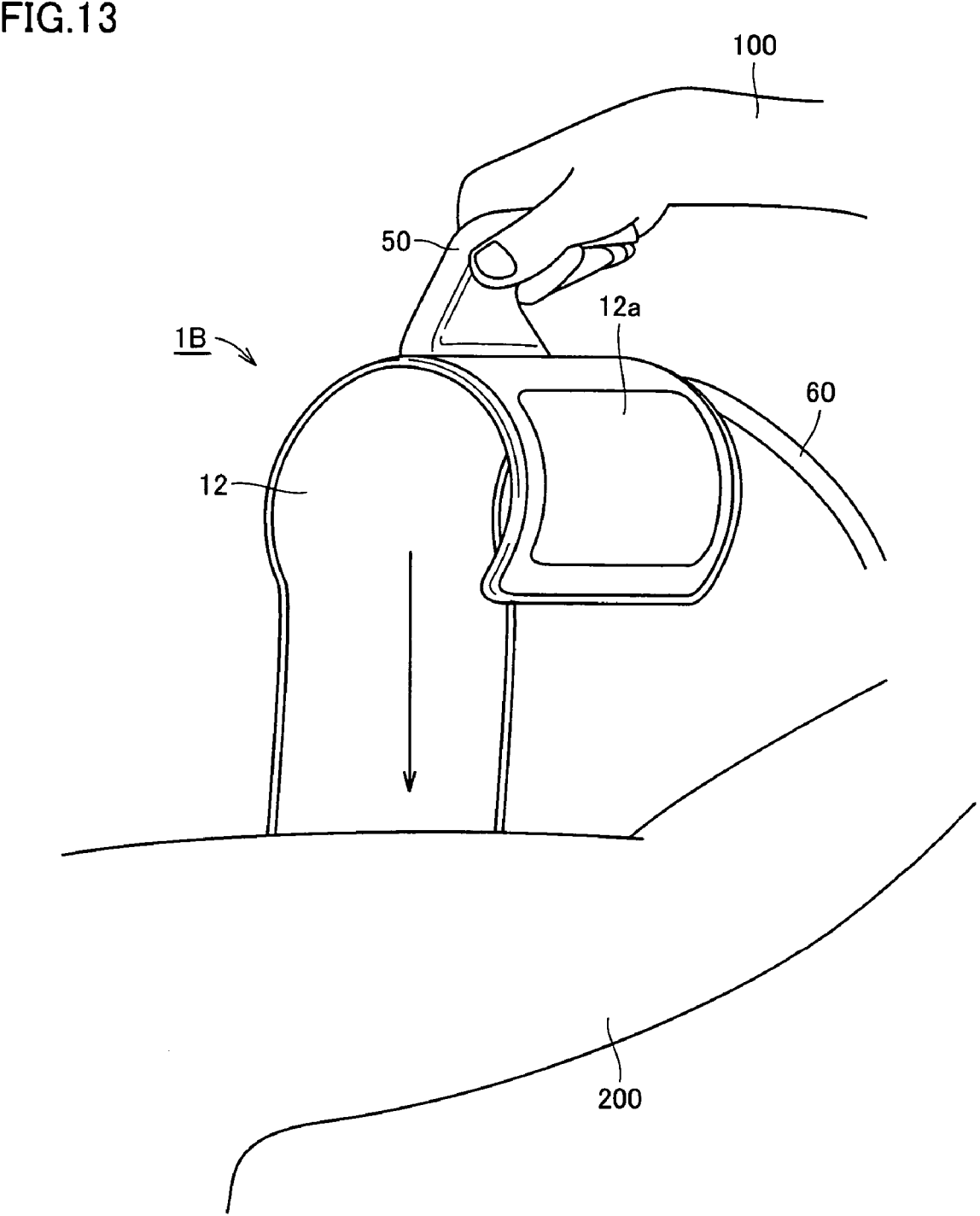
FIG. 13 is a schematic diagram illustrating how the cuff for a blood pressure monitor of the second embodiment is fitted to an upper arm.

FIG. 13 schematically illustrates how the cuff for a blood pressure monitor of the second embodiment of the present invention is fitted to an upper arm. As shown in FIG. 13, in the state where the subject is gripping handle 50 with the right hand 100 and manipulating lever 52 provided at handle 50 with the fingers except for the thumb of the right hand 100, curled elastic member 22 is in the diameter-increased state, with the hollow portion of curled elastic member 22 being radially expanded, as described above. In this state, the subject inserts the upper arm of the left hand 200 into the hollow portion via the slit-like opening of cuff main unit 10 and places cuff main unit 10 at a prescribed position of the left, upper arm. The subject then relaxes the fingers manipulating lever 52 to make it return to the initial position, thereby releasing the manipulation of lever 52.

In response, the pulled-up state of wire 41 by pull-up portion 42a1 of pivoting member 42 serving as the pull-up mechanism is released, and curled elastic member 22 having been in the diameter-increased state is decreased in diameter by its own elastic force, so that the cross sectional area of the hollow portion of cuff main unit 10 is decreased. However, the measurement site of the upper arm is positioned in the hollow portion of cuff main unit 10, which restricts the reduction of the diameter to a certain extent. This achieves the state where air bag 20 is pressed against the upper arm with an appropriate pressing force by curled elastic member 22. After this state is obtained, the subject releases the right hand 100 from handle 50, winds the extension portion of cover member 12 around the upper arm, and secures the extension portion of cover member 12 to velcro fastener 12a to thereby maintain the above-described state.

Figure 14:
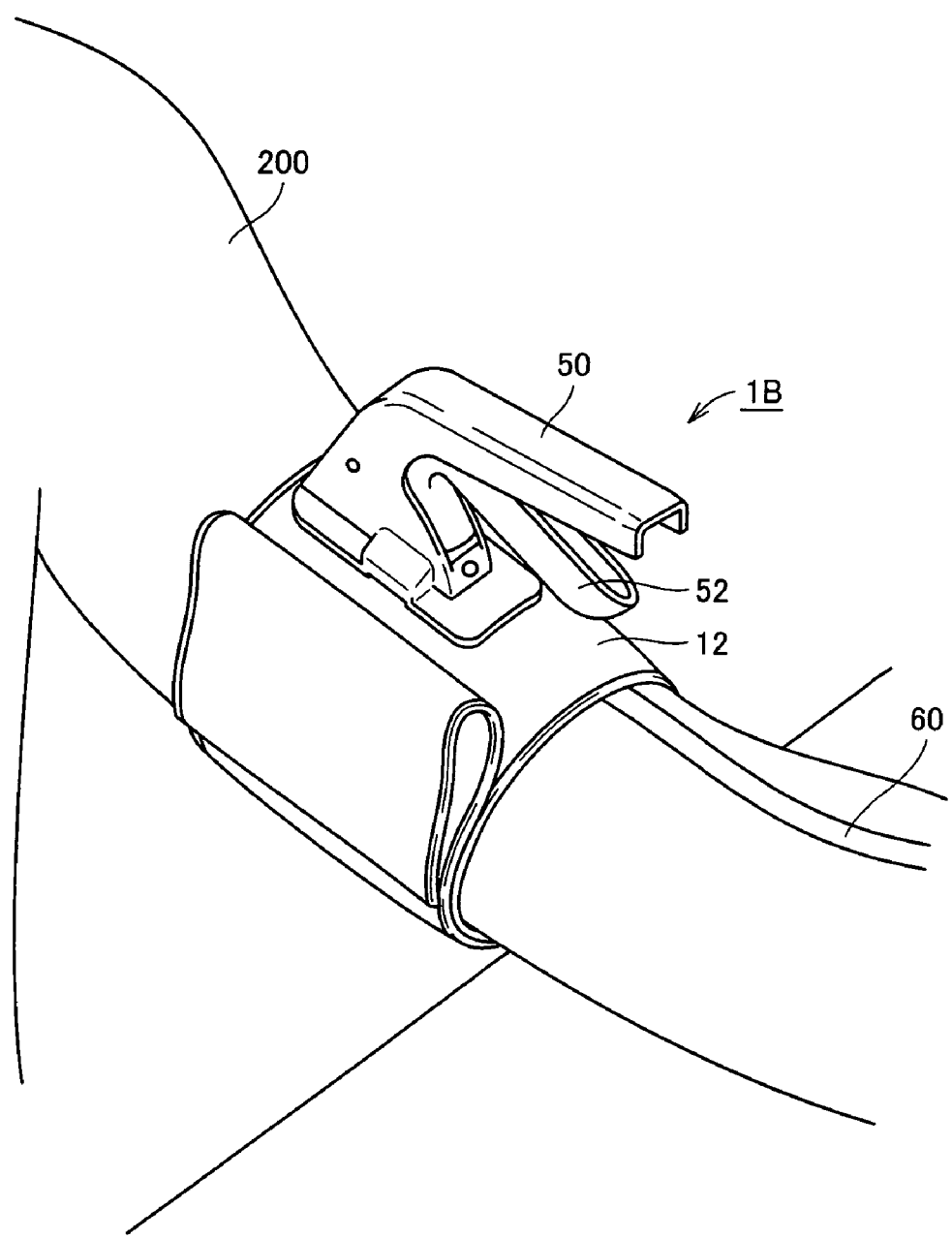
FIG. 14 is a perspective view showing the state where the cuff for a blood pressure monitor of the second embodiment is fitted to an upper arm.

FIG. 14 shows in perspective view the state where the cuff for a blood pressure monitor of the present embodiment is fitted to the upper arm. As the subject performs the above-described series of manipulations, the diameter increasing/decreasing mechanism incorporated in cuff main unit 10 operates in the above-described manner and, as shown in FIG. 14, cuff main unit 10 is fitted to the upper arm of the subject with an appropriate fastening force. In this state, the pressurized air is delivered from the main unit of the blood pressure monitor via rubber tube 60 to air bag 20, which tightens air bag 20 around the upper arm, so that the artery located inside the upper arm is pressed to enable measurement of the blood pressure values.

In the above-described cuff 1B for a flood pressure monitor of the present embodiment, the mechanical elements including wire 41, pivoting member 42 and others constituting the diameter increasing/decreasing mechanism work in cooperation with each other to increase and decrease the diameter of curled elastic member 22 that is the elastic member. In other words, the mechanical elements constituting the diameter increasing/decreasing mechanism function as the diameter-forcibly-increasing mechanism for forcibly increasing the diameter of curled elastic member 22. The mechanical elements implementing the diameter-forcibly-increasing mechanism work in association with the manipulation of lever 52 that is the manipulation portion provided at handle 50.

In the above-described cuff 1B for a blood pressure monitor of the present embodiment, lever 52 serving as the manipulation portion for switching the operation of the diameter increasing/decreasing mechanism is provided at handle 50 that is the member gripped by the hand when fitting the cuff. This makes it possible to perform gripping of handle 50 and manipulation of lever 52 simultaneously with the hand other than the one on which cuff main unit 10 is being mounted. Accordingly, it is possible to fit cuff 1B for a blood pressure monitor on the measurement site of the upper arm in one step with a single hand, ensuring outstanding ease of handling upon fitting. As a result, the fitting operation becomes easy even for elderly people and women relatively weak in physical strength. Further, since the fitting operation is easy, it is relatively easy to mount cuff main unit 10 at an appropriate position on the upper arm, which reduces occurrence of measurement errors due to displacement of the fitted position, thereby enabling accurate measurement of the blood pressure values. Still further, since curled elastic member 22 presses air bag 20 against the upper arm with an appropriate pressing force, accurate measurement of the blood pressure values can be realized repeatedly. Accordingly, cuff 1B for a blood pressure monitor having the above-described configuration can implement a cuff for a blood pressure monitor that can readily be fitted and ensures accurate and stable measurement of blood pressure values.

In cuff 1B for a blood pressure monitor of the present embodiment, handle 50 is preferably arranged on the outer peripheral surface of cuff main unit 10 at a location corresponding to the position of the artery in the upper arm around which cuff main unit 10 is wound. With this configuration, the handle serves as an indicator for accurate positioning of cuff main unit 10, thereby facilitating fitting of the cuff on the appropriate position.

In cuff 1B for a blood pressure monitor of the present embodiment, in the state where cuff main unit 10 is fitted on the upper arm, handle 50 may be gripped with the right hand 100 and lever 52 may be manipulated with the fingers of the right hand 100 except for the thumb to increase the diameter of curled elastic member 22, to dismount cuff main unit 10 from the left hand 200, and then the manipulation of lever 52 may be released. This permits dismounting of cuff 1B for a blood pressure monitor from the measurement site of the upper arm in one step. As such, great ease of handling is ensured not only for mounting but also for dismounting of the cuff.

Although the case of employing the lever as the manipulation portion in cuff 1B for a blood pressure monitor of the second embodiment has been explained above by way of example, the manipulation portion may be a slide button or a dial button, or may be the push-button as in the first embodiment described above. Further, although the case of arranging the lever serving as the manipulation portion under the handle has been explained in the second embodiment, the position for arrangement of the manipulation portion is not restricted thereto. The manipulation portion may be arranged at any position of the handle. Further, the position for arrangement of the manipulation portion is not restricted to the position on the handle, but it may be arranged on the cuff main unit in the vicinity of the handle. All that is needed is that the manipulation portion is arranged in a position that enables manipulation thereof with the hand holding the handle.

Further, the configuration of the diameter increasing/decreasing mechanism is not restricted to the one explained above. The diameter increasing/decreasing mechanism of any configuration may be employed, as long as the diameter of the curled elastic member that is the elastic member can be increased or decreased in association with manipulation of the manipulation portion. In the case where the curled elastic member is formed of a plurality of segments and elastic bodies and the diameter increasing/decreasing mechanism is configured to pull up the segments located at the respective ends in the circumferential direction in the radially outward direction using the line-shaped or band-shaped member such as a wire as described above, the curled elastic member is preferably configured with three or more segments. With such a configuration, outstanding ease of handling when fitting the cuff (particularly excellent manipulability when increasing/decreasing the diameter of the curled elastic member) is ensured, compared to the case of the cuff for a blood pressure monitor as in the above-described conventional example 4 having the curled elastic member divided into halves. Accordingly, it is possible to provide a cuff for a blood pressure monitor that can readily be handled by even elderly people and women relatively weak in physical strength.

Furthermore, each of the diameter-increasing operation and the diameter-decreasing operation does not necessarily have to be done in association with a single manipulation (manipulation of the lever, and release thereof). For example, the diameter-increasing operation may be done with manipulation of the first time, and the diameter-decreasing operation may be done with manipulation of the second time. It is also possible to configure the diameter-increasing operation and the diameter-decreasing operation to be achieved in association with separate manipulation portions.

In the above-described first and second embodiments, the case of fitting the cuff on the left upper arm and gripping the handle and manipulating the manipulation portion with the right hand has been explained. However, it is of course possible to grip the handle and manipulate the manipulation portion with the left hand and fit the cuff on the right upper arm. Further, although the cuff for the so-called upper arm blood pressure monitor that is mounted on the upper arm for measurement of the blood pressure values has been explained by way of example in the first and second embodiments, the present invention is not restricted thereto, but is of course applicable to a cuff for a so-called wrist blood pressure monitor that is mounted on the wrist for measurement of the blood pressure values, or a cuff for a so-called ankle blood pressure monitor that is mounted on the ankle for measurement of the blood pressure values.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A cuff for a blood pressure monitor fitted to a measurement site of a living body for measurement of a blood pressure value, comprising:
   a cuff main unit wound around the measurement site to be fitted on the living body, wherein said cuff main unit includes:
   a fluid bag for pressing the living body,
   an elastic member wound annularly on the outside of said fluid bag and changeable in size in a radial direction, and
   a diameter increasing/decreasing mechanism for increasing/decreasing a diameter of said elastic member wherein said diameter increasing/decreasing mechanism includes a diameter-decreased state maintaining mechanism for maintaining said elastic member in a diameter-decreased state by restricting elastic deformation of said elastic member in a radially outward direction, a diameter-decreased state releasing mechanism for releasing said elastic member to a diameter-increased state by releasing the restriction of the elastic deformation of said elastic member by said diameter-decreased state maintaining mechanism, and a diameter-forcibly-decreasing mechanism for forcibly decreasing the diameter of said elastic member in opposition to an elastic force of said elastic member in the diameter-increased state, and
   each of said diameter-decreased state maintaining mechanism, said diameter-decreased state releasing mechanism and said diameter-forcibly-decreasing mechanism works in association with manipulation of a manipulation portion;

a handle provided on an outer peripheral surface of said cuff main unit and gripped with a hand for fitting of the cuff; and wherein said manipulation portion is provided at said handle or at said cuff main unit in the vicinity of said handle, wherein said manipulation portion increases/decreases the diameter of said elastic member by switching an operation of said diameter increasing/decreasing mechanism.

2. The cuff for a blood pressure monitor according to claim 1, wherein said manipulation portion is a push-button.

3. The cuff for a blood pressure monitor according to claim 1, wherein said manipulation portion is a lever.

4. The cuff for a blood pressure monitor according to claim 1, wherein said manipulation portion is a push-button provided at said handle, said diameter-decreased state releasing mechanism works in association with depression of said push-button to cause said elastic member having been maintained in the diameter-decreased state by said diameter-decreased state maintaining mechanism to be released to the diameter-increased state, and said diameter-forcibly-decreasing mechanism and said diameter-decreased state maintaining mechanism work in association with release of the depression of said push-button to forcibly decrease the diameter of said elastic member and to cause said elastic member forcibly decreased in diameter to be maintained in the diameter-decreased state.

5. The cuff for a blood pressure monitor according to claim 1, wherein said diameter increasing/decreasing mechanism includes a diameter-forcibly-increasing mechanism for forcibly increasing the diameter of said elastic member in opposition to an elastic force of said elastic member in a radially inward direction, and said diameter-forcibly-increasing mechanism works in association with manipulation of said manipulation portion.

6. The cuff for a blood pressure monitor according to claim 5, wherein said manipulation portion is a lever provided at said handle, said diameter-forcibly-increasing mechanism works in association with manipulation of said lever to forcibly increase the diameter of said elastic member in the diameter-decreased state, and said diameter-forcibly-increasing mechanism stops working in association with release of the manipulation of said lever, so that said elastic member in the diameter-increased state is decreased in diameter.

7. A cuff for a blood pressure monitor fitted to a measurement site of a living body for measurement of a blood pressure value, comprising:

a cuff main unit wound around the measurement site to be fitted on the living body, wherein said cuff main unit includes:

a fluid bag for pressing the living body, an elastic member wound annularly on the outside of said fluid bag and changeable in size in a radial direction, and a diameter increasing/decreasing mechanism for increasing/decreasing a diameter of said elastic member wherein said diameter increasing/decreasing mechanism includes a fastening band wound on the outside of said elastic member, a pair of movable members attached to respective ends in the circumferential direction of said fastening band and movable along the circumferential direction of said cuff main unit, an elastic body elastically connecting said movable members, and a lock member working in association with manipulation of a manipulation portion and capable of locking said movable members in an immovable manner in opposition to an elastic force of said elastic body;

a handle provided on an outer peripheral surface of said cuff main unit and gripped with a hand for fitting of the cuff, wherein the manipulation portion provided at said handle or at said cuff main unit in the vicinity of said handle, wherein said manipulation portion increases/decreases the diameter of said elastic member by switching an operation of said diameter increasing/decreasing mechanism.

8. A cuff for a blood pressure monitor fitted to a measurement site of a living body for measurement of a blood pressure value, comprising:

a cuff main unit wound around the measurement site to be fitted on the living body, wherein said cuff main unit includes:

a fluid bag for pressing the living body, an elastic member wound annularly on the outside of said fluid bag and changeable in size in a radial direction, and a diameter increasing/decreasing mechanism for increasing/decreasing a diameter of said elastic member wherein said diameter increasing/decreasing mechanism includes a line-shaped or band-shaped member provided along the outside of said elastic member and having its ends attached to the corresponding ends in the circumferential direction of said elastic member, and a pull-up mechanism capable of pulling up an approximately central part of said line-shaped or band-shaped member in a direction coming apart from the outer surface of said elastic member;

a handle provided on an outer peripheral surface of said cuff main unit and gripped with a hand for fitting of the cuff; and a manipulation portion provided at said handle or at said cuff main unit in the vicinity of said handle, wherein said manipulation portion increases/decreases the diameter of said elastic member by switching an operation of said diameter increasing/decreasing mechanism.

9. The cuff for a blood pressure monitor according to claim 8, wherein said elastic member includes at least three segments arranged along the circumferential direction, and elastic bodies each located between neighboring ones of said segments and connecting the neighboring segments with each other, and said line-shaped or band-shaped member has its ends attached to the pair of segments located at the respective ends in the circumferential direction of said elastic member.

* * * * *